(12) United States Patent
Emrick et al.

(10) Patent No.: US 8,895,688 B2
(45) Date of Patent: Nov. 25, 2014

(54) HALOGEN-FREE FLAME RETARDING MATERIALS BASED ON BISPHENOL TRIAZOLE RESINS AND POLYMERS

(75) Inventors: Todd Emrick, South Deerfield, MA (US); Beom-Young Ryu, Dong-gu (KR)

(73) Assignee: University of Masschusetts, Boston, MA (US)

( * ) Notice: Subject to any disclaimer, the term of this patent is extended or adjusted under 35 U.S.C. 154(b) by 198 days.

(21) Appl. No.: 13/489,490

(22) Filed: Jun. 6, 2012

(65) Prior Publication Data
US 2012/0316313 A1     Dec. 13, 2012

Related U.S. Application Data

(60) Provisional application No. 61/494,299, filed on Jun. 7, 2011.

(51) Int. Cl.
| | |
|---|---|
| C07D 249/06 | (2006.01) |
| C08G 65/40 | (2006.01) |
| C07D 407/12 | (2006.01) |
| C08G 63/685 | (2006.01) |
| C07D 405/14 | (2006.01) |
| C07D 403/14 | (2006.01) |
| C08G 73/08 | (2006.01) |

(52) U.S. Cl.
CPC ............ *C07D 405/14* (2013.01); *C07D 407/12* (2013.01); *C08G 63/6856* (2013.01); *C07D 403/14* (2013.01); *C08G 73/08* (2013.01); *C07D 249/06* (2013.01)
USPC ........... 528/168; 528/172; 528/176; 528/191; 528/210; 548/255

(58) Field of Classification Search
None
See application file for complete search history.

(56) References Cited

PUBLICATIONS

Ryu and Emrick, "Thermally Induced Structural Transformation of Bisphenol-1,2,3-triazole Polymers: Smart, Self-Extinguishing Materials," Angewandte Chemie International Edition, vol. 49, Nov. 9, 2010, pp. 9644-9647.*
Ryu and Emrick, "Bisphenol-1,2,3-triazole (BPT) Epoxies and Cyanate Esters: Synthesis and Self-Catalyzed Curing," Macromolecules, vol. 44, Jun. 21, 2011, pp. 5693-5700.*

\* cited by examiner

*Primary Examiner* — Robert Sellers
(74) *Attorney, Agent, or Firm* — Milstein Zhang & Wu LLC

(57) ABSTRACT

The invention provides halogen-free, bisphenol triazole resins and polymers having exceptional flame retarding properties, related compositions and methods of making and use thereof.

17 Claims, 11 Drawing Sheets

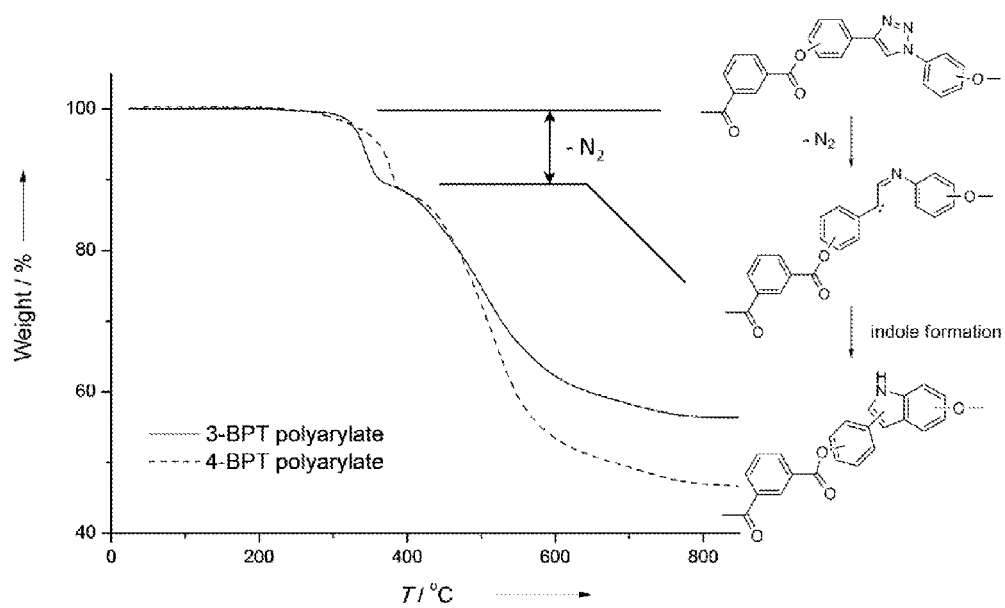
FIG. 1. TGA thermograms of 3-BPT and 4-BPT polyarylates (heating rate 10 °C/min in $N_2$).

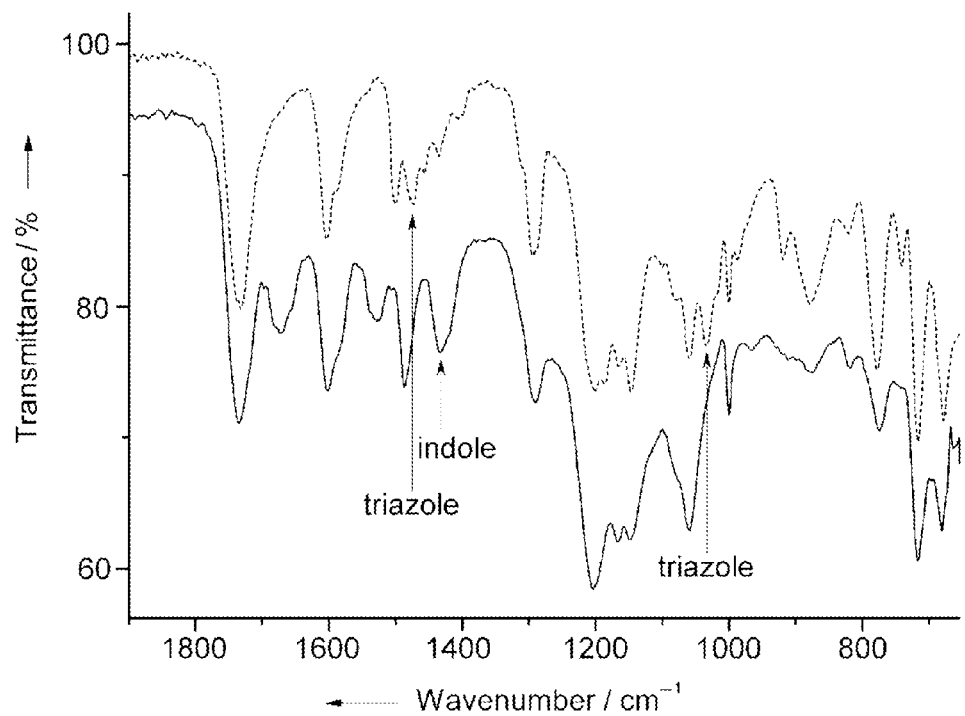
FIG. 2. FT-IR spectra of 3-BPT polymer 3 (dashed line), and the same polymer after heating at 350 °C for 10 minutes (solid line).

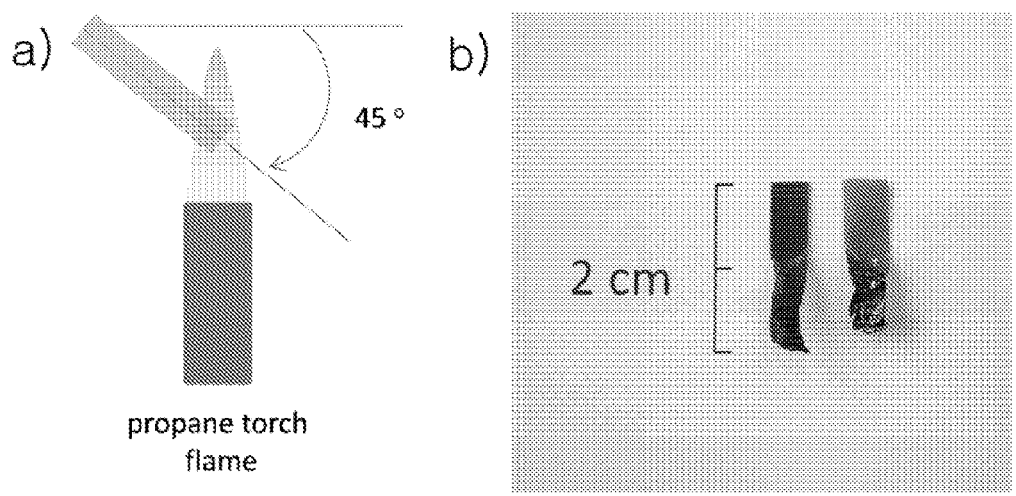
FIG. 3. a) Small scale flame test configuration; b) samples after the test (left: 3-BPT polyarylate; right: Kapton®).

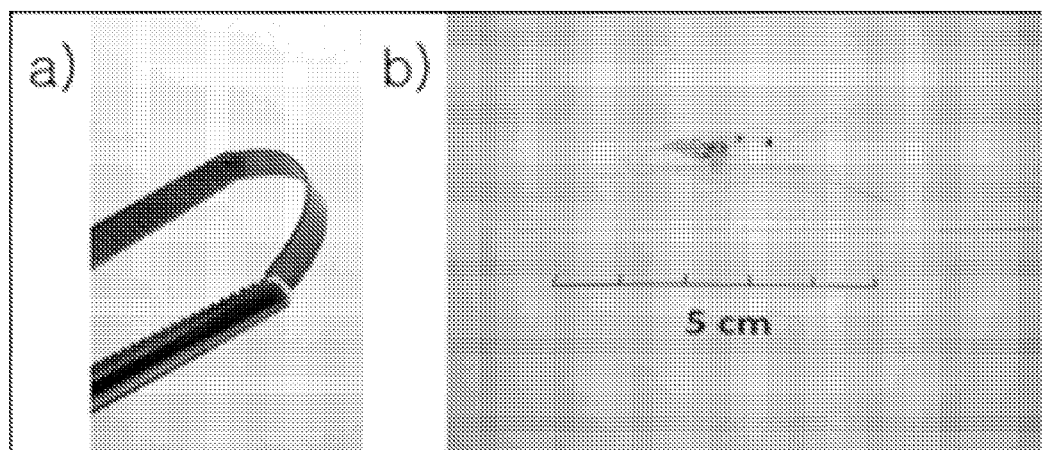
FIG. 4. a) 3-BPT polymer film formed by hot-pressing; b) 3-BPT fibers pulled from the melt.

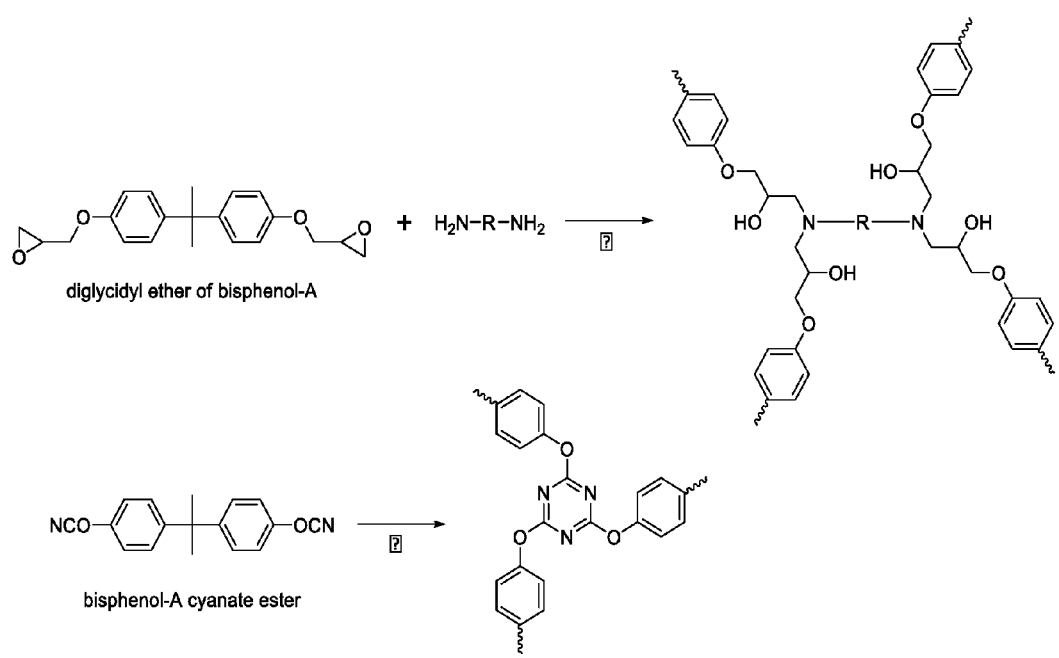
FIG. 5. Curing networks based on bisphenol-A epoxy (top) and bisphenol-A cyanate ester (bottom).

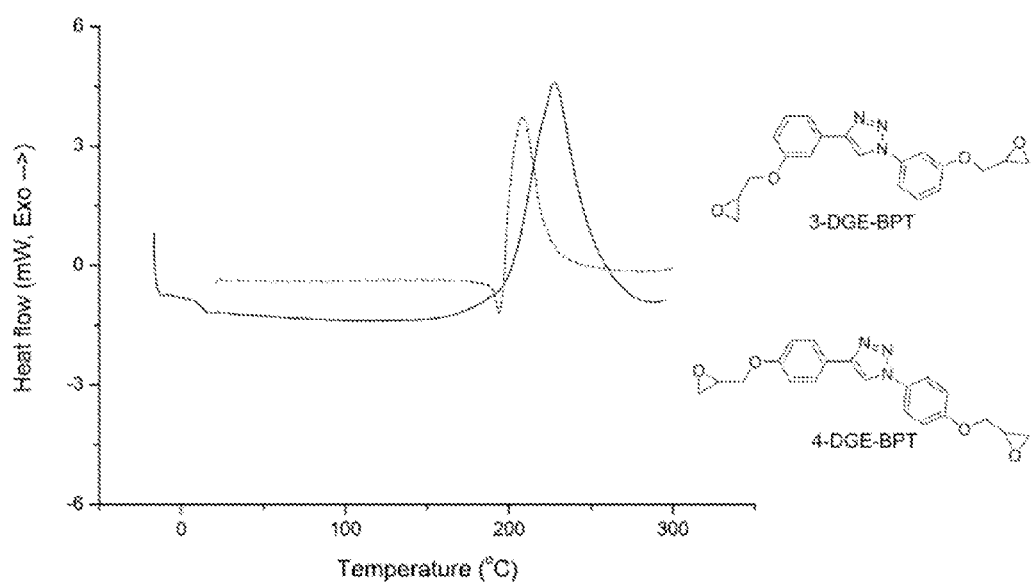
FIG. 6. DSC thermograms of 3-DGE-BPT (line) and 4-DGE-BPT (dot) resins.

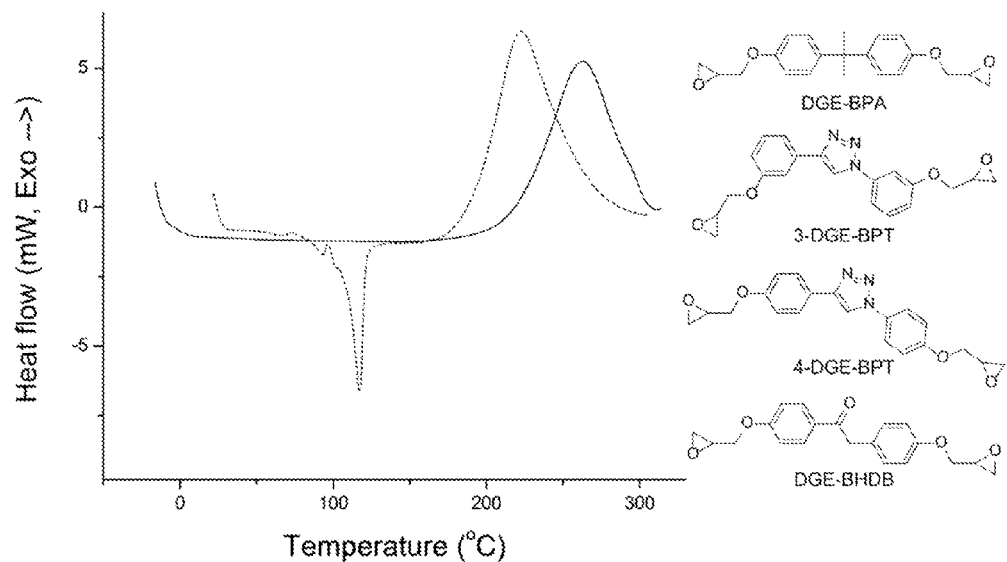
FIG. 7. DSC thermograms of DGE-BPA/3-DGEBPT (1/1, w/w, line) and DGE-BEDB/4-DGE-BPT (4/1, w/w, dot) blend.

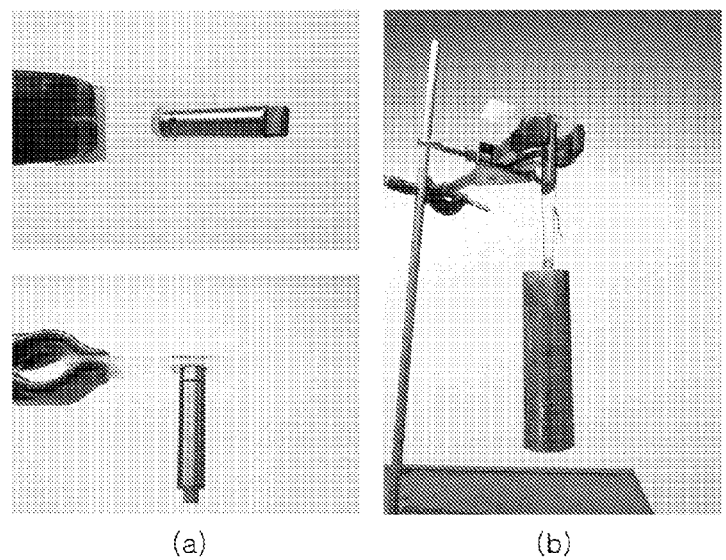
FIG. 8. Adhesion demonstration using the 3-DGE-BPT resin ((a) before loading additional weight and (b) after loading 700 g of metal weight).

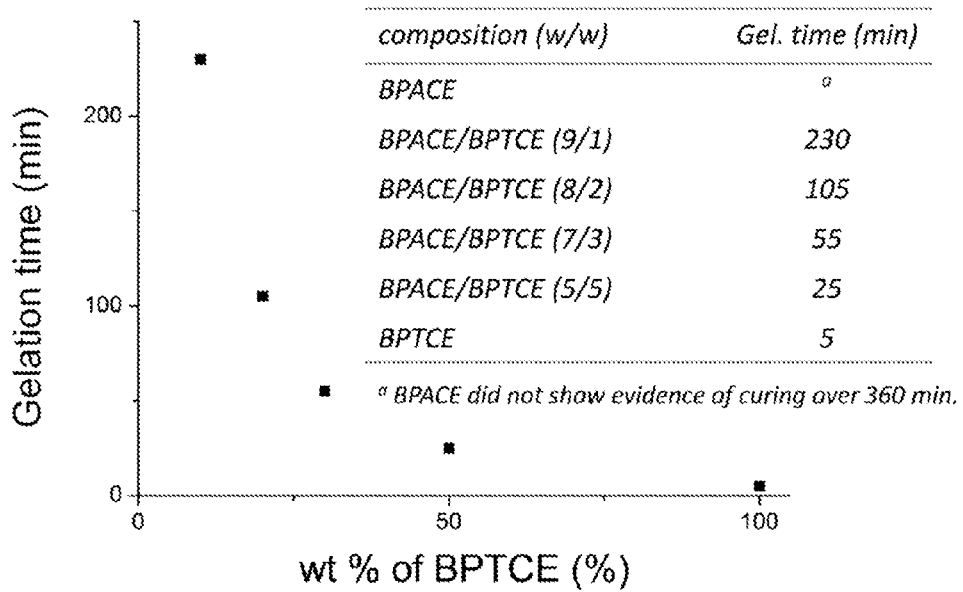
FIG. 9. Measured gelation time of BPACE, 3-BPTCE, and BPACE/BPTCE blends.

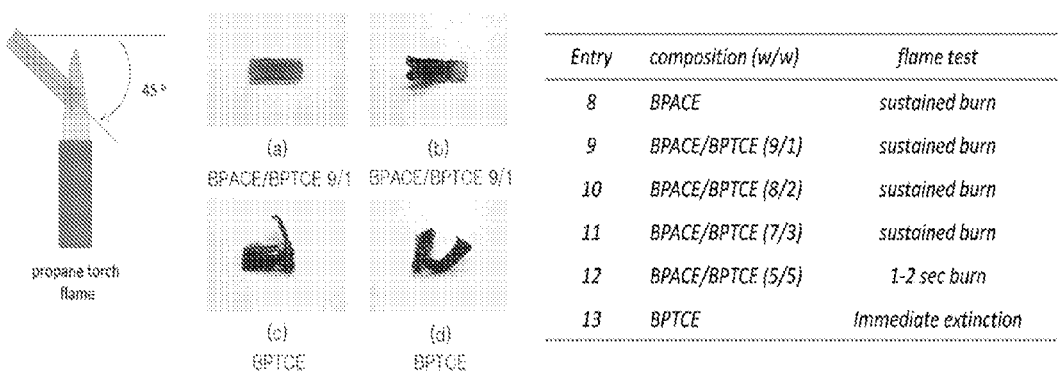
FIG. 10. Left: diagram of a small scale flame test; middle: the specimens (a) before test, and (b)-(d) after test; right: flame test results as a function of cyanate ester composition.

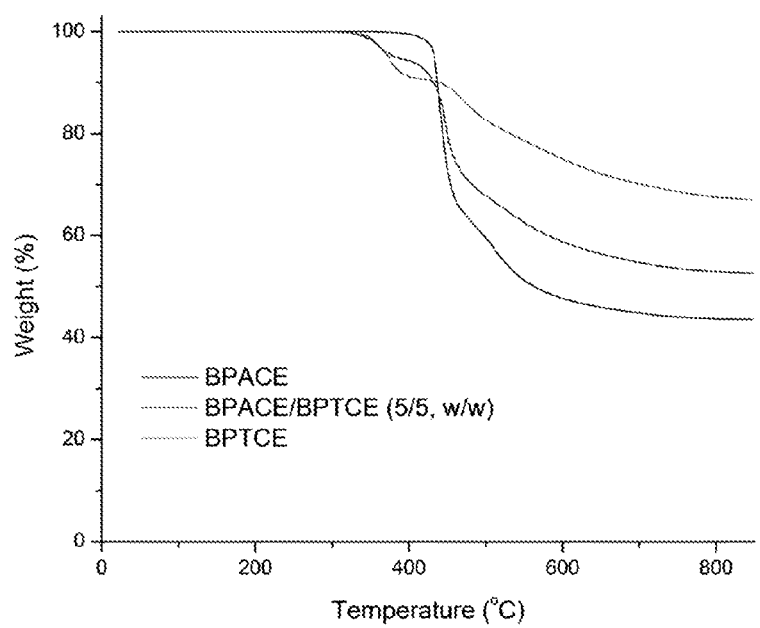
FIG. 11. TGA thermograms of cured BPACE (black), BPTCE (red), and BPACE/BPTCE (5/5, w/w, blue).

HALOGEN-FREE FLAME RETARDING MATERIALS BASED ON BISPHENOL TRIAZOLE RESINS AND POLYMERS

PRIORITY CLAIMS AND RELATED APPLICATIONS

This application claims the benefit of U.S. Provisional Application No. 61/494,299, filed Jun. 7, 2011, the entire content of which is expressly incorporated herein by reference.

GOVERNMENT RIGHTS

The United States Government has certain rights to the invention pursuant to Grant No. FAA-09-G-013 from Federal Aviation Administration to the University of Massachusetts.

FIELD OF THE INVENTION

The invention generally relates to monomers, polymers and polymer-based flame retarding materials. More particularly, the invention relates to halogen-free, bisphenol triazole compounds, epoxy and cyanate ester resins thereof, and related polymers (including co-polymers) having exceptional flame retarding and other desired properties, as well as methods of making and using the same.

BACKGROUND OF THE INVENTION

Polymers and polymerization methods provide important materials such as specialty plastics, foams, gels, and rubbery materials. Despite the many advances in the past decades realized through polymer chemistry, significant imperfections and challenges remain, for example, the aging and cracking of the materials and leaching of additives. (Stevens, M. P. 1990 in *Polymer Chemistry: an Introduction*, Oxford University Press, New York; Odian, G. 2004 in *Principles of Polymerization*, Wiely, New York; Murphy, J. 2001 in *Additives for Plastics Handbook*, Elsevier, New York.)

Environmental contamination and bioaccumulation of additives, such as flame-retardants, plasticizers, and anti-oxidants, are particularly problematic. Added inorganic salts compromise the physical/mechanical properties of polymers. Halogenated flame retardant additives are bio-accumulative, and thus threaten the environment and human health. (Blum, et al. 1997 *Science* 195, 17-23; Gold, et al. 1978 *Science* 200, 785-787; Fishbein, 1985 *Carcinog. Mutagens Envron.* 5, 75-93; de Boer, et al. 1998 *Nature* 394, 28-29; Hale, et al. 2001 *Nature* 412, 140-141; Rahman, et al. 2004 *Prog. Polym. Sci.* 29, 1223-1248; g) Gomara, et al. 2007 *Environ. Sci. Technol.* 41, 6961-6968; Blum 2007 *Science* 18, 194; Lyons, 1970 in *Chemistry and Uses of Fire Retardants*, Wiely, New York; Camino, et al. 2001 *Polym. Degrad. Stab.* 74, 457-464.)

Due to their excellent adhesive properties, processability and low cost, epoxy and cyanate ester resins are used prominently as polymer matrix composites. (Pilato, et al. 1994 *Advanced composite materials*; Springer, Berlin Heidelberg New York; Lee, et al. 1967 *Handbook of epoxy resins*; McGraw Hill, New York; McAdams, et al. 1988 *Encyclopedia of polymer science and engineering*; Wiley, New York, Vol. 6, p 322-382; Nair, et al. 2001 *Adv. Polym. Sci.* 155, 1-99.) For example, bisphenol-A (BPA) epoxy formulations dominate the epoxy resin market, but generally contain fillers, curing agents, and flame retardants (FRs). (Pham, et al. 2004 *Kirk-Othmer encyclopedia of chemical technology*; Wiley, New York, Vol. 10, p 347-461.) The inherent flammability of such materials is particularly problematic in settings that require flame resistance, such as vehicles, and electronic and construction materials. Brominated FR small molecules such as polybrominated diphenyl ethers, hexabromocyclododecane, and tetrabromobisphenol A (TBBPA) have been implemented widely to reduce flammability. (Levchik, et al. 2004 *Polym. Int.* 53, 1901-1929; Guerra, et al. 2011 *The Handbook of Environmental Chemistry: Introduction to brominated flame retardants: commercially products, applications, and physicochemical properties*; Springer, Berlin Heidelberg.) However, many brominated FRs were recently classed together with halogenated FRs, and present serious health and environmental concerns, such as bioaccumulation and associated carcinogenicity. Potential negative effects of such molecules on the environment, and in animals and humans, remain controversial and are under continued investigation. (*Communication from the commission on the risk evaluation and the risk reduction strategies for the substances*, C152, Official Journal of the European Union, 2008; Debenst, et al. 2010 *J. Environ. Monit.* 12, 1918-1923; McCormick, et al. 2010 *Aquatic Toxicology* 100, 255-262; de Wit, et al. 2011 *The Handbook of Environmental Chemistry: Emerging brominated flame retardants in the environment*; Springer, Berlin Heidelberg.)

Cyanate ester (CE) resins can cure thermally by cyclotrimerization to give polycyanurates, which exhibit high glass transition temperatures, toughness and low dielectric properties, making them useful in high performance structural and electronics applications. (Hamerton, I. (ed) 1994 *Chemistry and technology of cyanate ester resins*; Blackie Academic and Professional, Glasgow, UK.) Halogen-free CE resins (e.g., BPA, bisphenol-E, and bisphenol-M CE resin) exhibit undesirably high flammability, with a heat release capacity (HRC) of 240-320 J/(g-K), total heat release (THR) of 15-23 kJ/g, and char yield of 26-42%. (Lyon, et al. 2006 *Fire Mater.* 30, 89-106.) Moreover, the long gelation time of CE resins is frequently in need of adjustment through the addition of curing catalysts, such as imidazoles or transition metal complexes. (Fang, et al. 1995 *Progr. Polym. Sci.* 20, 61-118; Liu, et al. 1996 *Polymer* 37, 3675-3682.)

Thus, methods and materials that address the above problems are urgently needed. Novel polymer and synthetic methods that provide non-flammable properties in the absence of additives will benefit society in terms of both performance and safety.

SUMMARY OF THE INVENTION

The invention is based on the unexpected discovery of novel monomers and building blocks for halogen-free, bisphenol triazole resins and polymers that exhibit exceptional flame retarding properties, and the related compositions and methods of making and using the same.

In one aspect, the invention generally relates to a compound having the structural formula of:

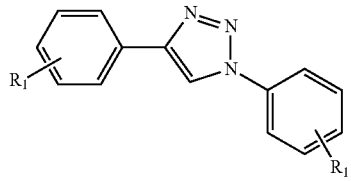

wherein $R_1$ is

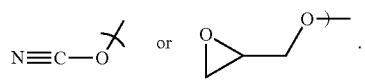

In another aspect, the invention generally relates to a polymer comprising a structural unit of:

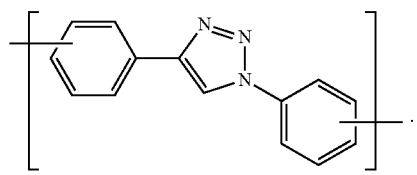

In some embodiments, the polymer further includes the structural unit of:

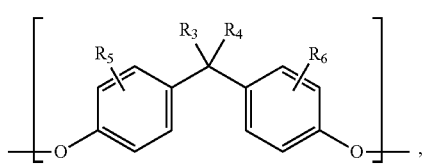

wherein
each of $R_3$ and $R_4$ is independently selected from hydrogen, unsubstituted $C_1$-$C_4$ alkyl, —$CF_3$, phenyl, and benzyl;
each of $R_5$ and $R_6$ is independently selected from hydrogen, unsubstituted $C_1$-$C_4$ alkyl, phenyl, and benzyl.

In some embodiments, the polymer further includes the structural unit of:

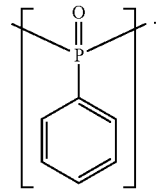

In yet another aspect, the invention generally relates to a polymer/random co-polymer having the structural formula of:

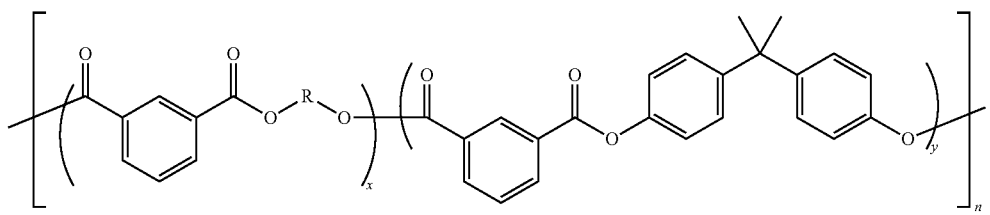

wherein R is

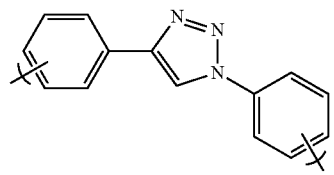

y is 0 or the molar ratio of x:y is in the range from about 0.1:0.9 to about 0.9:0.1 (x+y=1); and
n is from about 2 to about 200.

In yet another aspect, the invention generally relates to a polymer having the structural formula of:

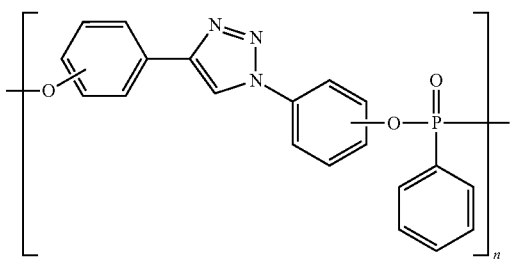

n is from about 2 to about 200.

In yet another aspect, the invention generally relates to a oligomer or polymer having the structural unit of:

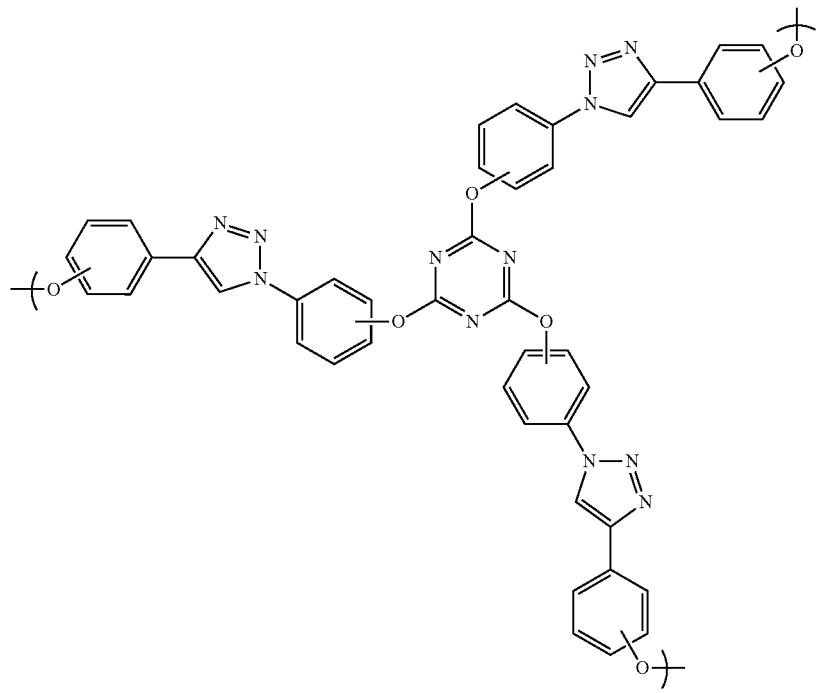

In some embodiments, the oligomer or polymer further includes the structural unit of:

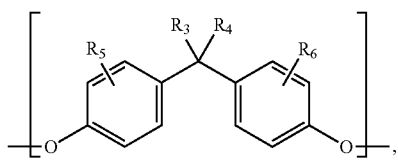

wherein each of $R_3$ and $R_4$ is independently selected from hydrogen, unsubstituted $C_1$-$C_4$ alkyl, —$CF_3$, phenyl, and benzyl;

each of $R_5$ and $R_6$ is independently selected from hydrogen, unsubstituted $C_1$-$C_4$ alkyl, phenyl, and benzyl.

The oligomer or polymer may include the structural unit of:

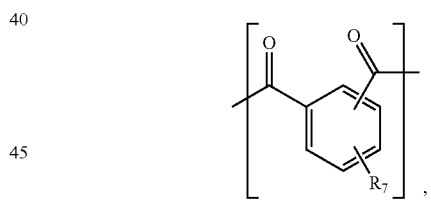

wherein $R_7$ is selected from hydrogen, unsubstituted $C_1$-$C_4$ alkyl, —$CF_3$, phenyl, and benzyl.

In yet another aspect, the invention generally relates to a method for preparing a co-polymer having the structural unit of:

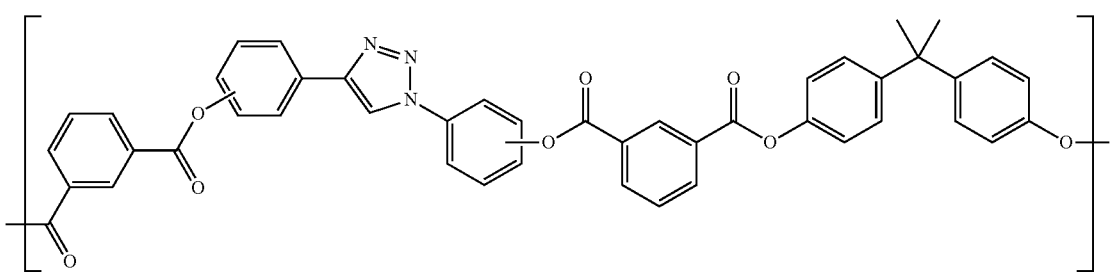

The method includes conducting a condensation polymerization as follows:

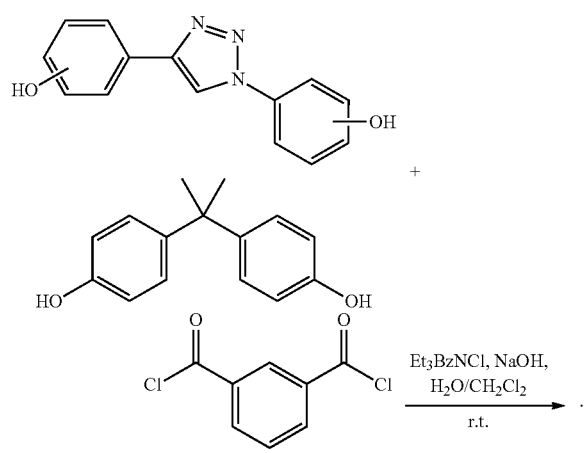

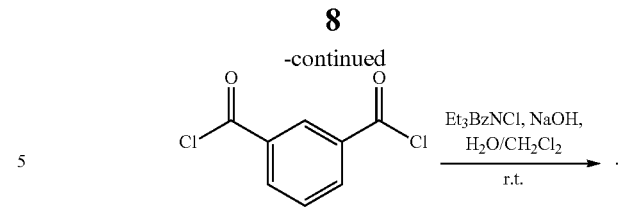

The diacidchloride may be any applicable structure capable of co-polymerizing with the other monomer(s). Similarly, the bisphenol comonomer may be any applicable bisphenol capable of co-polymerizing with the other co-monomer(s).

BRIEF DESCRIPTION OF THE DRAWINGS

FIG. 1 shows exemplary TGA thermograms of 3-BPT and 4-BPT polyarylates (heating rate 10° C./min in $N_2$).

FIG. 2 shows exemplary FT-IR spectra of 3-BPT polymer 3 (line), and the same polymer after heating at 350° C. for 10 minutes (dot).

FIG. 3 shows exemplary (a) Small scale flame test configuration; (b) samples after the test (left: 3-BPT polyarylate; right: Kapton®).

FIG. 4 shows exemplary (a) 3-BPT polymer film formed by hot-pressing; b) 3-BPT fibers pulled from the melt.

In yet another aspect, the invention generally relates to a method for preparing a random co-polymer having the structure of:

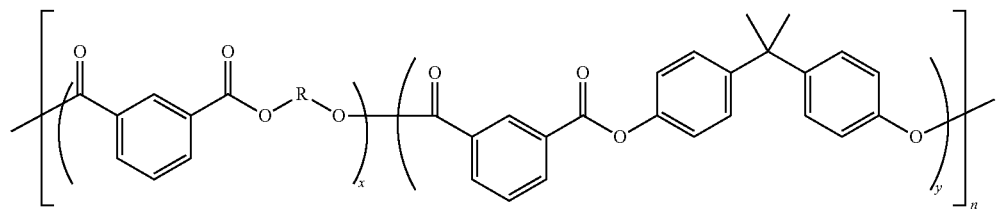

wherein R is

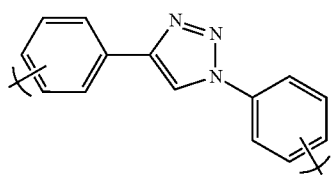

y is 0 or the x:y molar ratio is in the range from about 0.1:0.9 to about 0.9:0.1 (x+y=1); and n is from about 2 to about 200, wherein the co-polymer is a random copolymer. The method includes conducting the following polycondensation polymerization:

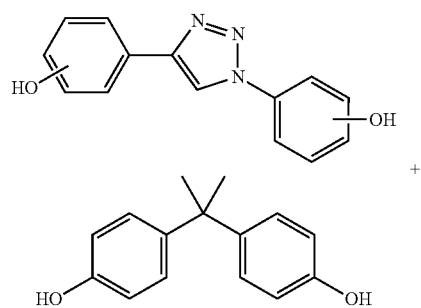

FIG. 5 shows exemplary curing networks based on bisphenol-A epoxy (top) and bisphenol-A cyanate ester (bottom).

FIG. 6 shows exemplary DSC thermograms of 3-DGE-BPT (line) and 4-DGE-BPT (dot) resins.

FIG. 7 shows exemplary DSC thermograms of DGE-BPA/3-DGEBPT (1/1, w/w, line) and DGE-BEDB/4-DGE-BPT (4/1, w/w, dot) blend.

FIG. 8 shows exemplary adhesion demonstration using the 3-DGE-BPT resin ((a) before loading additional weight and (b) after loading 700 g of metal weight).

FIG. 9 shows exemplary measured gelation time of BPACE, 3-BPTCE, and BPACE/BPTCE blends.

FIG. 10 shows exemplary (Left) diagram of a small scale flame test; middle: the specimens (a) before test, and (b)-(d) after test; right: flame test results as a function of cyanate ester composition.

FIG. 11 shows exemplary TGA thermograms of cured BPACE (black), BPTCE (red), and BPACE/BPTCE (5/5, w/w, blue).

DETAILED DESCRIPTION OF THE INVENTION

The invention disclosed herein provides novel halogen-free, bisphenol triazole (BPT) compounds, epoxy and cyanate ester resins thereof, and related polymers (including co-polymers) having exceptional flame retarding and other desired properties. For example, BPT-containing aromatic polyesters and polyphosphonates can be made by step-growth polymerization, giving para- and meta-linked structures. Characterization of the BPT-polymers revealed exceptional examples of high performance materials, which provide new opportunities in additive-free, non-flammable macromolecular materials.

Heat release capacity (HRC) is an inherent materials property, which is defined as the maximum specific heat release divided by the heating rate during a controlled thermal decomposition, and is now a well-established method for evaluating flammability characteristics of combustible materials. (Walters, et al. 2003 *J. Appl. Polym. Sci.* 87, 548-563; Lyon, et al. 2004 *J. Anal. Appl. Pyrolysis* 71, 27-46; Lyon, et al. 2006 *J. ASTM Int.* 3(4), 1-18; Wilkie, et al. 2006 *J. Mater. Chem.* 16, 2023-2030.) HRC is measured by a standard oxygen combustion calorimetry technique, and self-extinguishing properties are judged through performing small scale flame tests. (ASTM D7309-07, *Standard test method for determining flammability characteristics of plastics and other solid materials using microscale combustion calorimetry*.)

Gilchrist and coworkers reported on the conversion, by flash vacuum pyrolysis, of bisphenyl-1,2,3-triazoles to phenylindoles and nitrogen gas (Scheme 1). (Gilchrist, et al. 1975 *J. Chem. Soc. Perkin Trans.*1 1-8; Gilchrist, et al. 1975 *J. Chem. Soc. Perkin Trans.*1 8-11; Burgess, et al. 1968 *J. Am. Chem. Soc.* 90, 1923-1924; Kirmse 2002 *Eur. J. Org. Chem.* 2193-2256.) This organic structural rearrangement provides a new opportunity in polymer synthesis and materials application, but to our knowledge there is no prior report on the synthesis of polymers containing BPT in the backbone.

Scheme 1. Thermally-induced structural rearrangement of diphenyl-1,2,3-triazole.

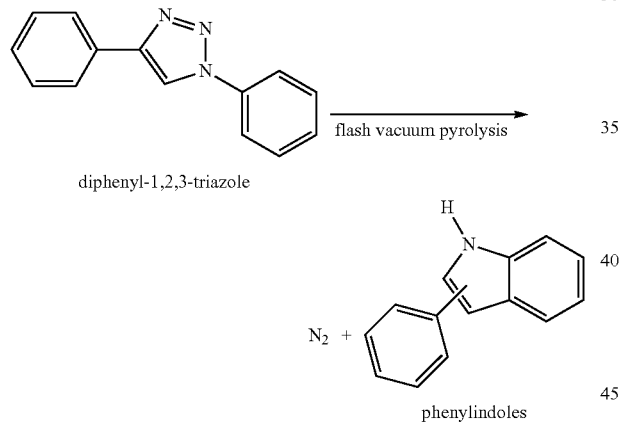

In one aspect, the invention generally relates to a compound having the structural formula of:

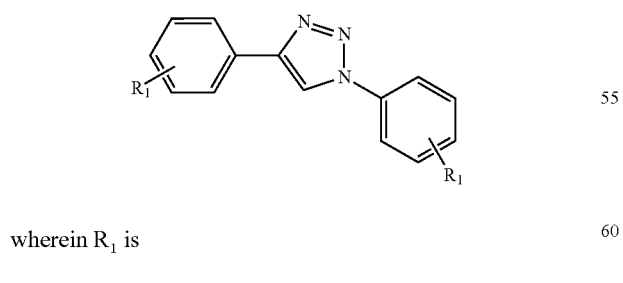

wherein $R_1$ is

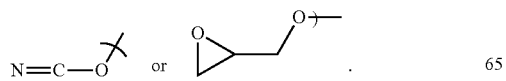

In some embodiments, the compound is:

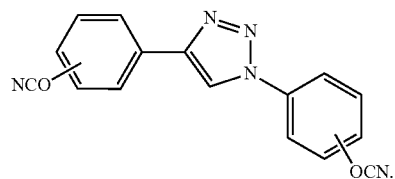

In certain preferred embodiments, the compound is:

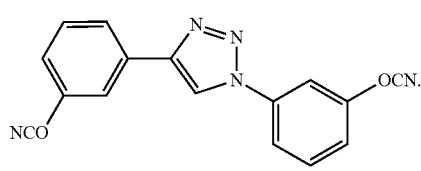

In certain preferred embodiments, the compound is:

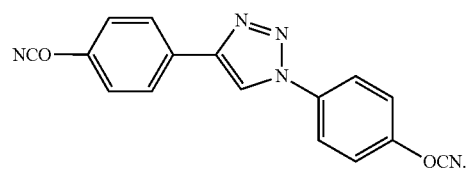

In some embodiments, the compound is:

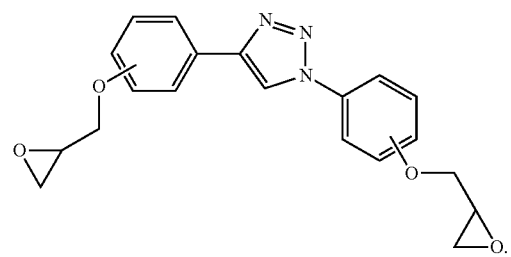

In certain preferred embodiments, the compound is:

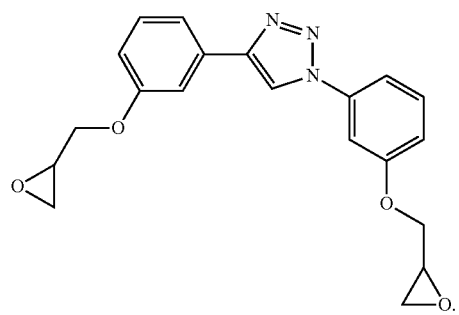 [SMILES: c1cc(OCC2CO2)cc(-c2cn(-c3cccc(OCC4CO4)c3)nn2)c1]

In certain preferred embodiments, the compound is:

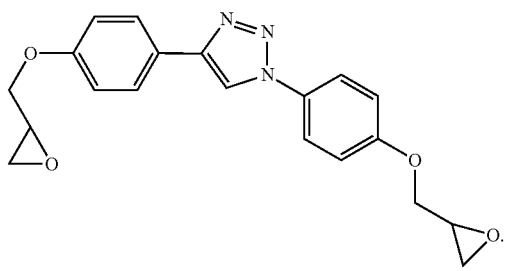 [SMILES: c1cc(-c2cn(-c3ccc(OCC4CO4)cc3)nn2)ccc1OCC1CO1]

In another aspect, the invention generally relates to a polymer that includes a structural unit of:

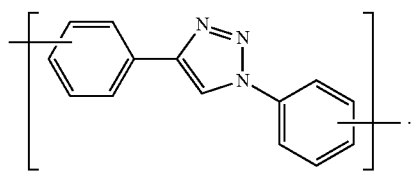

In certain preferred embodiments, the polymer includes a structural unit of:

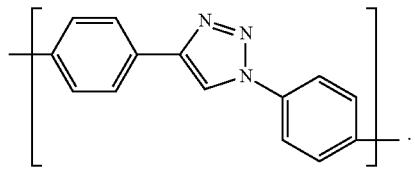

In certain preferred embodiments, the polymer includes a structural unit of:

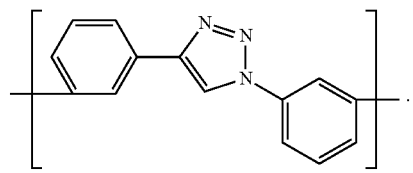

In some embodiments, the polymer further includes the structural unit of:

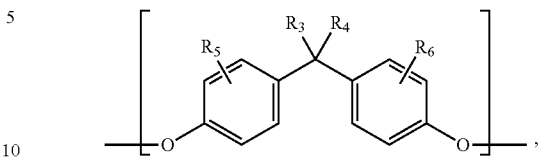

wherein
each of $R_3$ and $R_4$ is independently selected from hydrogen, unsubstituted $C_1$-$C_4$ alkyl, —$CF_3$, phenyl, and benzyl;

each of $R_5$ and $R_6$ is independently selected from hydrogen, unsubstituted $C_1$-$C_4$ alkyl, phenyl, and benzyl.

In certain preferred embodiments, each of $R_3$ and $R_4$ is methyl and $R_5$ and $R_6$ is hydrogen.

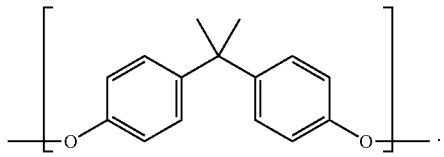

In some embodiments, the polymer includes a bifunctional group based on a bisphenol selected from the group consisting of 2,2-bis(4-hydroxyphenyl)propane (bisphenol A), 1,1-bis(4-hydroxyphenyl)-1-phenyl-ethane (bisphenol AP), 2,2-bis(4-hydroxyphenyl)hexafluoropropane (bisphenol AF), 2,2-bis(4-hydroxyphenyl)butane (bisphenol B), 2,2-bis(3-methyl-4-hydroxyphenyl)propane (bisphenol C), bis(4-hydroxyphenyl)-2,2-dichloroethane (bisphenol D), 1,1-bis(4-hydroxyphenyl)ethane (bisphenol E), bis(4-hydroxyphenyl)methane (bisphenol F), 2,2-bis(4-hydroxy-3-isopropylphenyl)propane (bisphenol G), 1,3-bis(2-(4-hydroxyphenyl)-2-propyl)benzene (bisphenol M) and bis(4-hydroxyphenyl)sulfone (bisphenol S). Thus, the polymer may be a co-polymer prepared with a co-monomer selected from Table 1.

TABLE 1

| Bisphenols useful as co-monomers | | |
|---|---|---|
| Structural formula | Name | Systematic name |
| HO—⌬—C(CH₃)₂—⌬—OH | Bisphenol A | 2,2-Bis(4-hydroxyphenyl)propane |
| HO—⌬—C(Ph)(CH₃)—⌬—OH | Bisphenol AP | 1,1-Bis(4-hydroxyphenyl)-1-phenyl-ethane |

TABLE 1-continued

| Bisphenols useful as co-monomers | | |
|---|---|---|
| Structural formula | Name | Systematic name |
| [structure] | Bisphenol AF | 2,2-Bis(4-hydroxyphenyl)hexafluoropropane |
| [structure] | Bisphenol B | 2,2-Bis(4-hydroxyphenyl)butane |
| [structure] | Bisphenol BP | Bis-(4-hydroxyphenyl)diphenylmethane |
| [structure] | Bisphenol C | 2,2-Bis(3-methyl-4-hydroxyphenyl)propane |
| [structure] | Bisphenol D | Bis(4-hydroxyphenyl)-2,2-dichlorethylene |
| [structure] | Bisphenol E | 1,1-Bis(4-hydroxyphenyl)ethane |
| [structure] | Bisphenol F | Bis(4-hydroxyphenyl)methane |

TABLE 1-continued

Bisphenols useful as co-monomers

| Structural formula | Name | Systematic name |
|---|---|---|
| | Bisphenol G | 2,2-Bis(4-hydroxy-3-isopropyl-phenyl)propane |
| | Bisphenol M | 1,3-Bis(2-(4-hydroxyphenyl)-2-propyl)benzene |
| | Bisphenol S | Bis(4-hydroxyphenyl)sulfone |

The polymer may include the structural unit of:

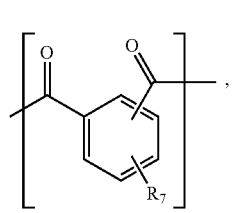

wherein $R_7$ is selected from hydrogen, unsubstituted $C_1$-$C_4$ alkyl, —$CF_3$, phenyl, and benzyl.

In certain preferred embodiments, $R_7$ is hydrogen.

In certain preferred embodiments, the structural unit is:

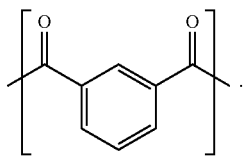

In certain preferred embodiments, the structural unit is:

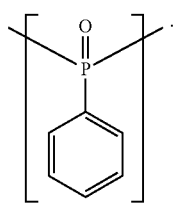

In some embodiments of the polymer, the molar ratio of:

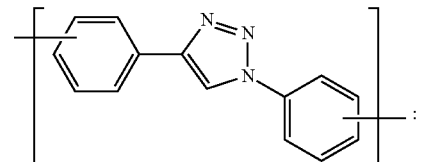

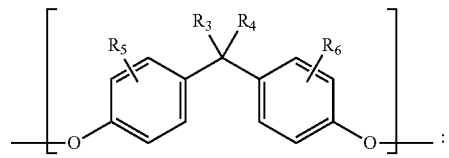

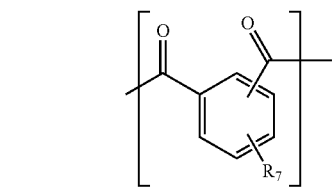

may be in the range from about 1:4:5 to about 4:1:5 (e.g., from about 1.5:3.5:5 to about 3.5:1.5:5; from about 2:3:5 to about 3:2:5, about 1:1:2).

In some embodiments of the polymer, the following structural unit is not present:

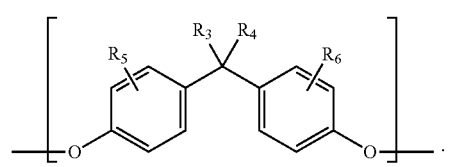

In some embodiments, the polymer includes the structural unit of:

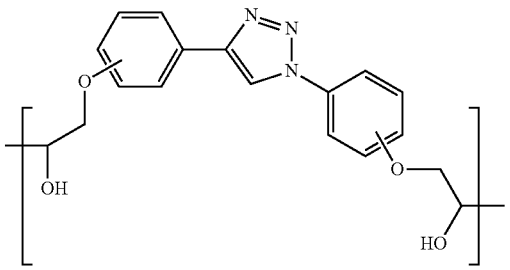

In certain preferred embodiments, the polymer includes the structural unit of:

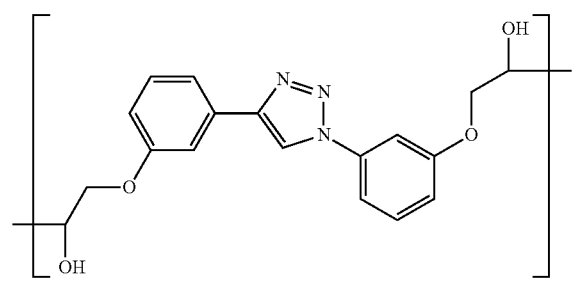

In certain preferred embodiments, the polymer includes the structural unit of:

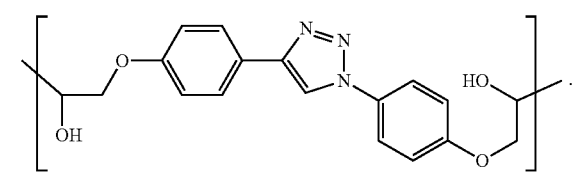

In yet another aspect, the invention generally relates to a polymer/random co-polymer having the structural formula of:

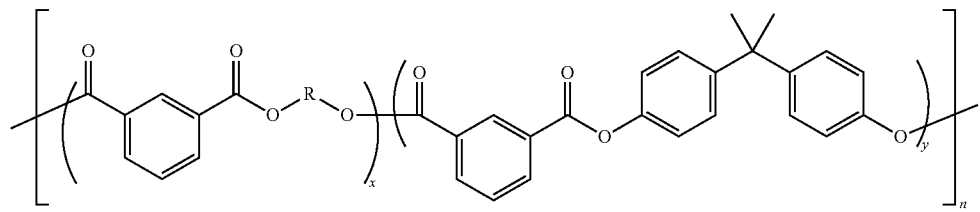

wherein R is

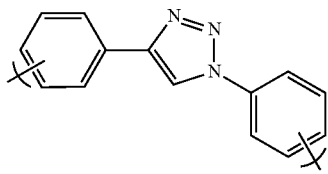

y is 0 or the x:y molar ratio (x+y=1) is in the range from about 0.1:0.9 to about 0.9:0.1 (e.g., from about 0.2:0.8 to about 0.8:0.2, from about 0.3:0.7 to about 0.7:0.3, from about 0.4:0.6 to about 0.6:0.4, about 0.5:0.5); and n is from about 2 to about 200.

In certain preferred embodiments, R is

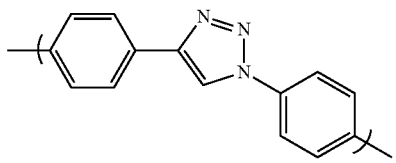

In certain preferred embodiments, R is

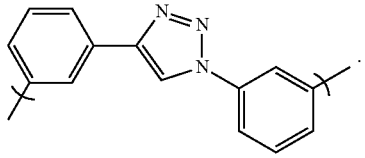

In some embodiments, y is zero. In some embodiments, y is 0.5.

In yet another aspect, the invention generally relates to a polymer having the structural unit of:

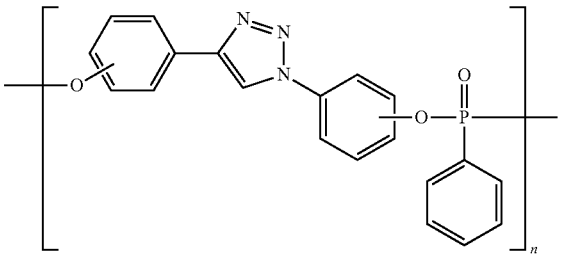

n is from about 2 to about 200 (e.g., about 5, about 10, about 25, about 50, about 100, about 150).

In yet another aspect, the invention generally relates to a oligomer or polymer having the structural unit of:

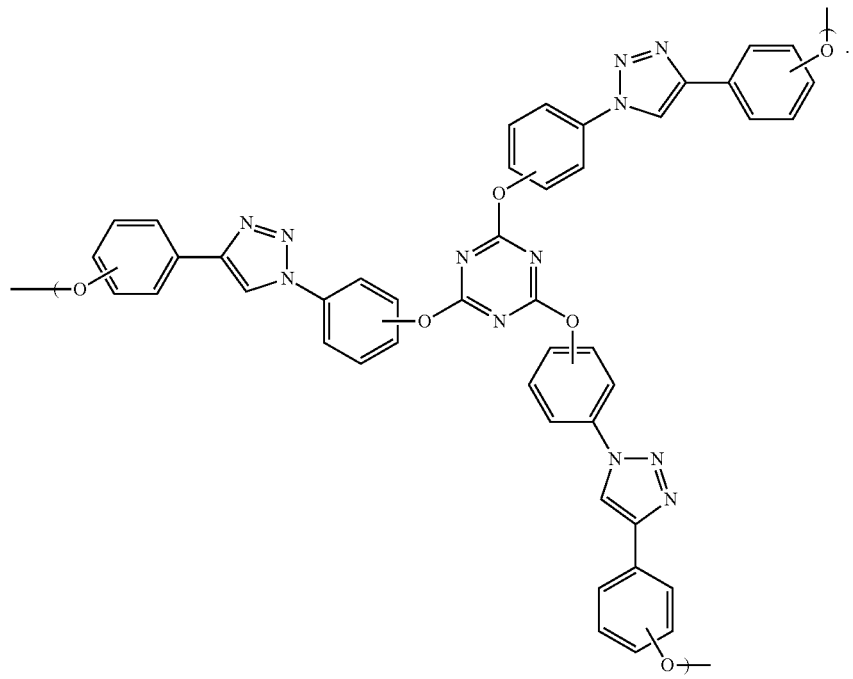

In some embodiments, the oligomer or polymer further includes the structural unit of:

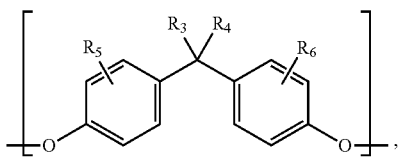

wherein
each of $R_3$ and $R_4$ is independently selected from hydrogen, unsubstituted $C_1$-$C_4$ alkyl, —$CF_3$, phenyl, and benzyl;
each of $R_5$ and $R_6$ is independently selected from hydrogen, unsubstituted $C_1$-$C_4$ alkyl, phenyl, and benzyl.

In certain preferred embodiments, each of $R_3$ and $R_4$ is methyl and $R_5$ and $R_6$ is hydrogen.

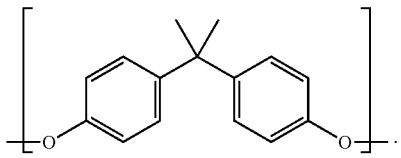

In some embodiments, the oligomer or polymer includes a bi-radical group based on a bisphenol selected from Table 1.

The oligomer or polymer may include the structural unit of:

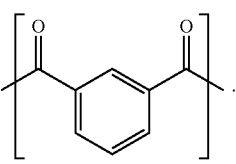

wherein $R_7$ is selected from hydrogen, unsubstituted $C_1$-$C_4$ alkyl, —$CF_3$, phenyl, and benzyl.

In certain preferred embodiments, $R_7$ is hydrogen.
In certain preferred embodiments, the structural unit is:

The polymer or co-polymer (or oligomer) of the invention may have a heat release capacity of less than about 400 J/g-K (e.g., less than about 350 J/g-K, less than about 300 J/g-K, less than about 250 J/g-K, less than about 200 J/g-K, in the range from about 200 J/g-K to about 400 J/g-K, in the range from about 200 J/g-K to about 300 J/g-K, in the range from about 300 J/g-K to about 400 J/g-K).

The polymer or co-polymer (or oligomer) of the invention may have an average molecular weight greater than about 5,000 g/mol (e.g., from about 5,000 g/mol to about 1,000,000 g/mol, from about 5,000 g/mol to about 500,000 g/mol, from about 5,000 g/mol to about 250,000 g/mol, from about 5,000 g/mol to about 100,000 g/mol, from about 5,000 g/mol to about 50,000 g/mol, greater than about 50,000.)

The polymer or co-polymer (or oligomer) of the invention may have a polydispersity indices from about 1 to about 6 (e.g., from about 2 to about 6, from about 2 to about 5, from about 3 to about 6). In some embodiments, the polymer or co-polymer (or oligomer) of the invention have a polydispersity indices greater than about 6.

The polymer or co-polymer (or oligomer) of the invention may have a solubility in N,N-dimethylformamide (DMF) from about 0 mg/mL to about 300 mg/mL (e.g., from about 0.01 mg/mL to about 300 mg/mL, from about 0.1 mg/mL to about 300 mg/mL, from about 1.0 mg/mL to about 300 mg/mL, from about 10 mg/mL to about 300 mg/mL, from about 50 mg/mL to about 300 mg/mL). In some embodiments, the polymer or co-polymer (or oligomer) of the invention have a solubility in DMF greater than about 300 mg/mL In yet another aspect, the invention generally relates to a method for preparing a co-polymer having the structural unit of:

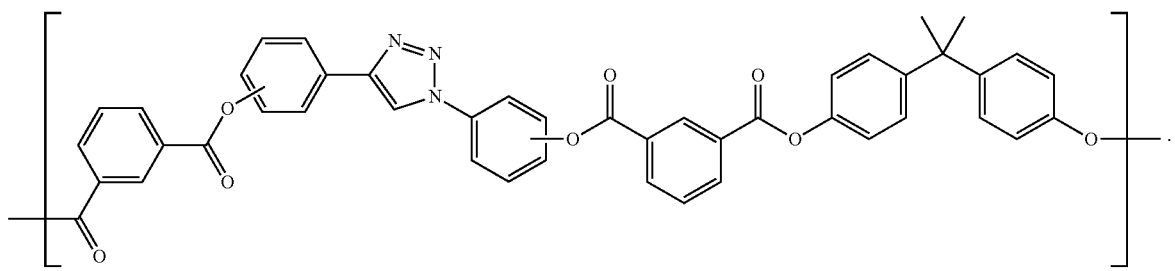

The method includes conducting a polycondensation polymerization as follows:

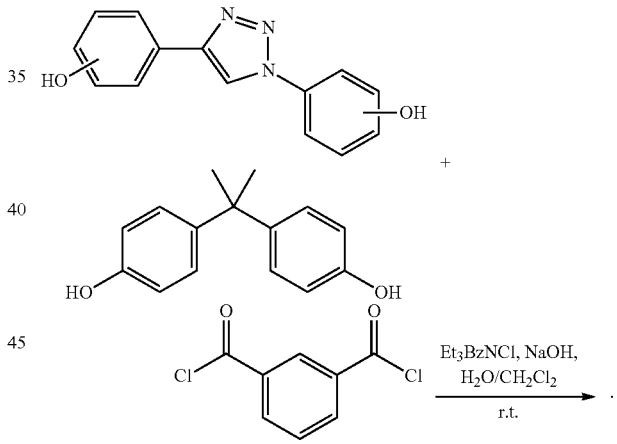

The diacid chloride may be any applicable diacid capable of co-polymerizing with the other monomer(s), for example,

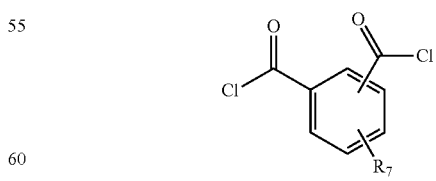

wherein $R_7$ is selected from hydrogen, unsubstituted $C_1$-$C_4$ alkyl, —$CF_3$, phenyl, and benzyl. Similarly, the bisphenol may be any applicable bisphenol capable of co-polymerizing with the other co-polymer(s), for examples, those shown in Table 1.

In yet another aspect, the invention generally relates to a method for preparing a random co-polymer having the structure of:

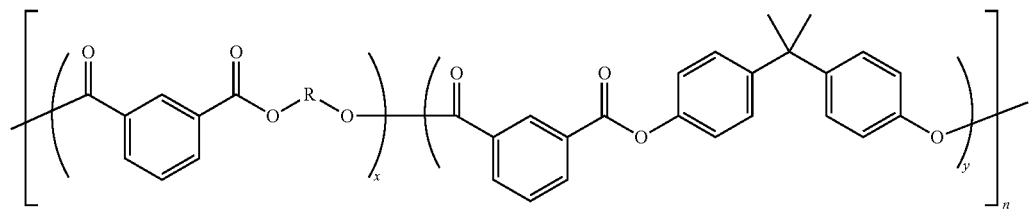

wherein R is

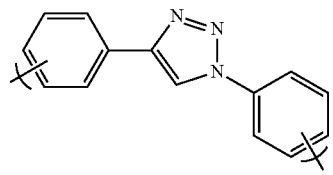

y is 0 or the x:y molar ratio is in the range from about 0.1:0.9 to about 0.9:0.1 (x+y=1); and n is from about 2 to about 200, wherein the co-polymer is a random copolymer. The method includes conducting the following polycondensation polymerization:

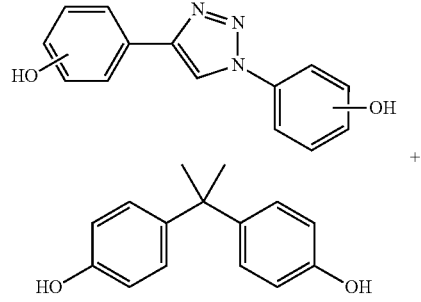

+

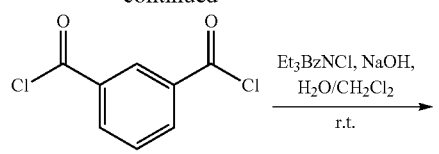

Examples

Scheme 2 shows the preparation of BPT-containing aromatic polyesters from the corresponding BPT monomer precursors. The phenyl azide and trimethylsilylethynyl (TMSE) precursors to monomers 1 and 2 were connected by copper catalyzed click cycloaddition, using CuBr and 2,2'-bipyridyl, in polar solvents such as DMF, to give the desired bis-phenolic triazole structures. (Pirali, et al. 2007 *ChemMedChem* 2, 437-440; Courme, et al. 2008 *Tetrahedron Lett.* 49, 4542-4545.) Recrystallization from acetic acid/water gave 4-BPT 1, and 3-BPT 2, in 60-70% yield, in sufficiently pure form to use directly in polymerization chemistry.

Scheme 2. Synthetic procedures for BPT polymers.

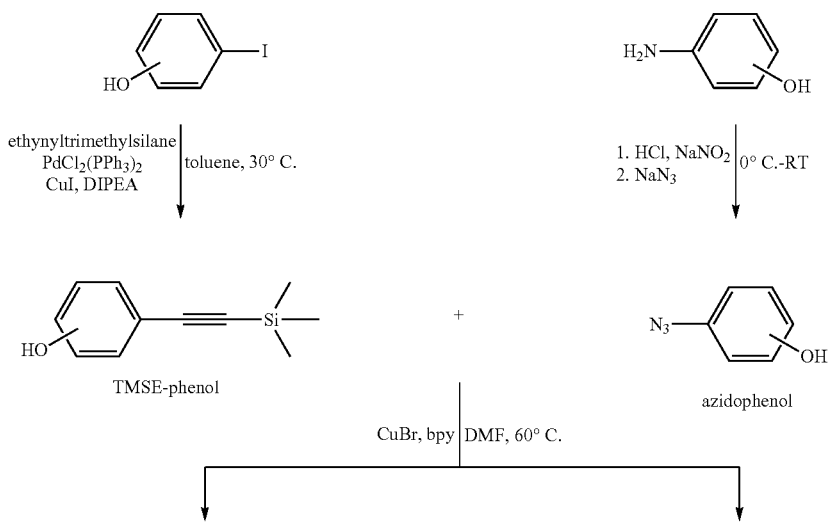

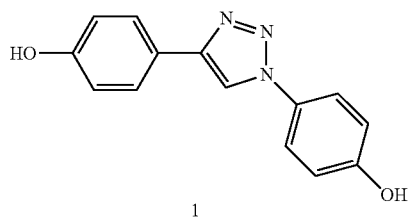

1
1,4-bis(4-hydroxyphenyl)-1,2,3-triazole (4-BPT)

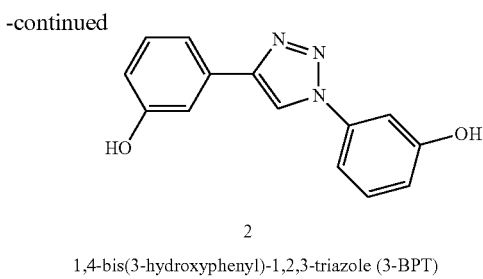

2
1,4-bis(3-hydroxyphenyl)-1,2,3-triazole (3-BPT)

-continued

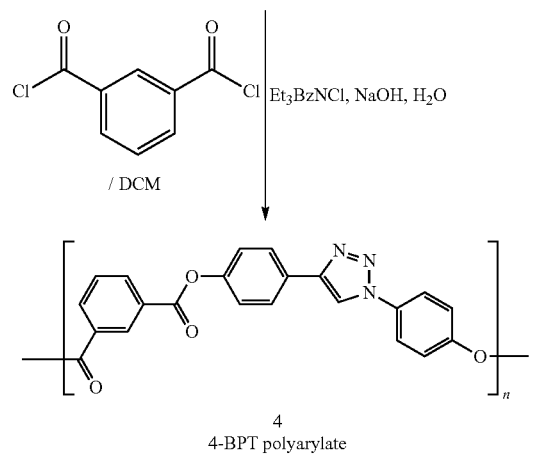

4
4-BPT polyarylate

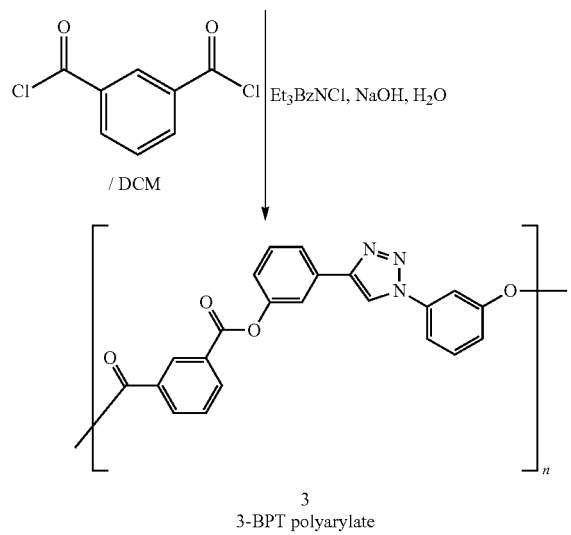

3
3-BPT polyarylate

BPT-containing polymers were prepared by interfacial polycondensation of BPT monomers 1 or 2 with isophthaloyl dichloride as the difunctional comonomer, benzyltriethylammonium chloride as the phase-transfer catalyst, and $CH_2Cl_2$ as the organic phase. Typical of interfacial polymerization, a film was seen to develop in the stirring heterogeneous reaction mixture during the course of the polymerization, indicating successful polymer formation at the fluid-fluid interface. The 4-BPT aromatic polyesters isolated from this reaction (~65% yield on ~1 gram scale) were found to be poorly soluble in common solvents (e.g., tetrahydrofuran, DMF, and N-methyl-2-pyrrolidone), making spectroscopic characterization difficult. Thus, the interfacial polymerization experiments were performed using bisphenol A as a comonomer with BPT and isophthaloyl chloride, in attempts to improve the solubility and processability of the BPT-containing materials. However, these copolymers proved only partially soluble, and also difficult to characterize. Nonetheless, thermal characterization of these 4-BPT polymers (which does not require solubility) was particularly promising, revealing exceptionally low heat release capacity (HRC) values of <50 J/g-K, and total heat release (THR) values of <7 kJ/g. This data, obtained by pyrolysis combustion flow calorimetry (PCFC), an oxygen consumption technique, places these novel BPT aromatic polyesters in the ultra-low flammability category, despite the absence of additives. (Walters, et al. 2003 *J. Appl. Polym. Sci.* 87, 548-563; Lyon, et al. 2004 *J. Anal. Appl. Pyrolysis* 71, 27-46; Lyon, et al. 2006 *J. ASTM Int.* 3(4), 1-18.)

Thermogravimetric analysis (TGA) of the 4-BPT polyarylates showed a two-step weight loss curve (about 12% weight loss at 300-400° C.), which would be expected from the initial structural rearrangement (resulting in loss of $N_2$), and a 47% char yield (i.e., residual mass after burning) at 850° C. Taken together, this outstanding set of thermal properties compelled us to investigate routes to more soluble, processable BPT-containing polymers, without resorting to the addition of flexible hydrocarbon chains that would improve solubility, but also markedly increase the heat release, and reduce char yield.

In order to increase the processability of BPT-containing polymers without compromising their exceptional thermal properties, 3-substituted BPT polyarylates were prepared. This was intended to exploit the kinked (and thus less rigid) structure of the meta-substituted 3-BPT framework, relative to the linear, para-substituted, 4-BPT case. Under interfacial polymerization conditions similar to those used for 4-BPT, the isolated yields of the 3-BPT/isophthaloyl chloride aromatic polyesters, and their copolymers with BPA, were in the 85-90% range. Fortunately, the solubility of the 3-BPT polymers was improved markedly over the 4-BPT materials, exhibiting excellent solubility in N-methyl-2-pyrrolidone (NMP) (~100 mg mL$^{-1}$). Moreover, 1:1 3-BPT:BPA copolyarylates were soluble in DMF, tetrachloroethane (TCE), and NMP. The 3-BPT/BPA copolymer compositions tracked closely to the monomer ratio introduced to the organic phase at the outset of the polymerization (as confirmed by $^1$H NMR spectroscopy).

The molecular weights and polydispersity indices (PDIs) of the 3-BPT polymers were estimated by gel permeation chromatography (GPC) against polystyrene calibration standards, eluting with NMP (0.05 M of LiCl) at 80° C. The 3-BPT polymers isolated from five different reaction batches showed number-average molecular weight ($\overline{Mn}$) values in the range of 9,800-10,900 g/mole, weight-average molecular weights ($\overline{Mw}$) in the range of 27,600-30,900 g/mole, and PDI values of 2.5-2.9. Similar molecular weights were achieved in the 3-BPT/BPA copolymerizations, for example $\overline{Mn}$=7,800 g/mol, $\overline{Mw}$=17,900 g/mol, and PDI~2.3.

Like the 4-BPT materials, 3-BPT-containing polymers and copolymers exhibited TGA curves that showed a two-step weight loss, reflecting loss of nitrogen ($N_2$) associated with conversion of the triazole moieties to indoles (FIG. 1). Interestingly, the char yield of the 3-BPT polymer observed at 850° C. was significantly higher (56%) than the 4-BPT materials (47%). The higher char yield of the meta-linked 3-BPT polymers may be attributed to its lower crystallinity and closer proximity of the phenyl rings, making it better suited for thermally-induced aromatization than the para-substituted structures. An analogous para vs. meta effect is seen in the commercial aromatic polyamides poly(p-phenylene terephthalamide) (Kevlar®) and poly(m-phenylene terephthalamide) (Nomex®). Kevlar® is highly crystalline, has excellent thermal stability (decomposition>500° C.), and high char yield, but heat release values significantly higher than those of Nomex® (Nomex® char yield=43% and heat release capacity=99 J/g-K; Kevlar® char yield=38% and heat release capacity=363 J/g-K). (Havelka-Rivard, et al. 1999 *Macromolecules* 32, 6418-6424; Yang, et al. 2010 *Polym. Degrad. Stab.* 95, 108-115; Allcock 1972 in *Phosphorus-nitrogen compounds*, Academic Press, New York, N.Y.; Lyon, et al. 2003 *Fire Mater.* 27, 195-208.) Clearly the meta-substitution provides a distinct advantage with regards to these key thermal properties, for both the commercial high performance polyamides and the novel BPT structures described here.

FIG. 2 shows the FT-IR spectra of 3-BPT polyarylate ($\overline{Mw}$=30,900 g/mole), before and after heating to 350° C. for 10 min. Notable changes in the FT-IR spectrum were seen after heating, between 1700 and 1000 $cm^{-1}$. Triazole signals at 1475 $cm^{-1}$ and 1035 $cm^{-1}$ (triazole ring stretching vibrations), were noticeably absent after heating, indicating the anticipated thermally-induced structural transformation. The appearance of an IR signal at 1435 $cm^{-1}$ (phenylindole skeletal vibrations) reflects the expected formation of phenylindole groups. In addition, at these high temperatures, some ester bond degradation should occur, as noted by the appearance of a carboxylate signal at 1670 $cm^{-1}$ in the spectrum. Pyrolysis gas chromatography-mass spectrometry (GC-MS) characterization of 3-BPT polyester 3, run at 400° C. for 6 min, revealed a gradual loss of $N_2$ and $CO_2$ in the 4-10 minute time-frame, and a sharp peak of isophthaloyl fragments at 24 min.

TABLE 2

Heat release capacity (HRC), total heat release (THR), and charring properties of BPT-containing polymers and commercial high-performance materials.

| Entry | Polymer | HRC (J/g-K) | THR (kJ/g) | Char (%)[b] |
|---|---|---|---|---|
| 1 | BPA polyarylate | 456 ± 13 | 17.7 ± 0.5 | 26 |
| 2 | 4-BPT/BPA (50/50) | 95 ± 4 | 12.0 ± 0.5 | 38 |
| 3 | 4-BPT | 46 ± 5 | 6.8 ± 0.3 | 47 |
| 4 | 3-BPT/BPA (50/50) | 102 ± 5 | 11.3 ± 0.4 | 44 |
| 5 | 3-BPT | 23 ± 3 | 4.6 ± 0.2 | 56 |
| 6 | Kevlar ®[a] | 363 ± 2 | 8.8 ± 0.5 | 38 |
| 7 | Nomex ®[a] | 99 ± 0.5 | 6.6 ± 0.2 | 43 |
| 8 | Kapton ®[a] | 14 | 4.0 | 66 |

[a]Data taken from the references. (Havelka-Rivard, et al. 1999 *Macromolecules* 32, 6418-6424; Yang, et al. 2010 *Polym. Degrad. Stab.* 95, 108-115; Allcock 1972 in *Phosphorus-nitrogen compounds*, Academic Press, New York, NY; Lyon, et al. 2003 *Fire Mater.* 27, 195-208.))
[b]Data obtained from TGA at 850° C. in nitrogen (heating rate 10° C./$min^{-1}$).

PCFC characterization of these 3-BPT aromatic polyesters exhibited a HRC of 23 J/g-K and THR of 4.5 kJ/g. Such low heat release values for hydrocarbon-based polymers are rare (lower even than inorganic-based polyphosphazenes), and these values for BPT structures rank very close to those of the aromatic polyimide Kapton®, one of the few commercialized ultra-low flammability polymers (Table 2). BPA/3-BPT copolymers, having an equimolar BPA:BPT ratio, gave a HRC of 102 J/g-K, and THR of 11.3 kJ/g. Thus, Entries 2 and 4 of Table 2 show that interrupting the BPT homopolymer structure with BPA units removes the influence of the meta- vs. para-substitution seen for the BPT homopolymers. Nonetheless, it is remarkable to observe that inserting 50% BPT as a comonomer in the classic BPA polymeric structure leads to a 400% reduction in HRC from BPA-only structures (i.e., compare Entries 1 and 4 in Table 2). In a small scale flame test (FIG. 4), conducted by placing a thin film (2×0.5×0.025) cm of 3-BPT polyarylate in a propane torch flame at a 45 degree angle for 5-10 seconds, the film was seen to extinguish immediately (i.e., self-extinguish) following removal from the flame, with little smoke evolution. In a propane torch flame, 3-BPT polyarylates charred immediately, and the char maintained its shape during the course of the test (i.e., without dripping).

To better understand these novel BPT-containing structures as materials, preliminary data associated with their mechanical properties was generated. Specimens for tensile tests ($\overline{Mw}$=30,900 g/mol, $T_{g=195}$° C.) were prepared by thermal pressing at 240° C. The ultimate strength, tensile modulus, and extension at break of 3-BPT/isophthaloyl chloride polymers were measured on an Instron (Model 5564) as 95±25 MPa, 2.5±0.3 GPa, and 4.5±0.6%, respectively. These properties, while unoptimized and derived from relatively low molecular weight polymer films, already demonstrate significant mechanical strength, with tensile strength intermediate between commercial BPA polyarylate (i.e., Ardel®, 69 MPa) and a commercial liquid crystalline aromatic copolyester (i.e., Xydar®, 110-135 MPa). (Dean 1996 in *Polymeric Materials Encyclopedia*, Vol. 8 (Eds: J. C. Salamone), CRC Press, Boca Raton, Fla., pp 5902-5909.) The mechanical properties of BPT-polyarylates (and other BPT-containing structures) were expected to improve as higher molecular weight samples are prepared and utilized. FIG. 3a shows a 3-BPT polymer sample ($\overline{Mn}$=10,900 g/mole $\overline{Mw}$=30,900 g/mole, 2×0.5×0.025 cm) as a thin, flexible film after processing by pressing at 240° C. Moreover, low molecular weight versions of BPT polymer 3 (i.e., $\overline{Mn}$=3,200 g/mole, $\overline{Mw}$=5,730 g/mole) readily formed fibers from the polymer melt (at 260° C.), by simply pulling the material with tweezers from the hot stage of a melting point apparatus (FIG. 4b). It is anticipated that blending of these structures with other fiber-forming polymers will permit additional opportunities in fiber-based applications. The 3-BPT structures prepared so far are advantageous for their amenability to both solution and thermal processing, and do not require special processing conditions needed for other materials such as polybenzoxazoles and polyimides, or polymer precursors as in the case of Kapton®.

Thus, novel BPT monomers and polymers were synthesized by click cycloaddition and interfacial polycondensation, and investigated their heat release and mechanical properties. This work shows that BPT homopolymers and copolymers are viable candidates for applications in which ultra-low flammability materials are needed. Further added benefit is derived from having such exceptional thermal properties without requiring additives of any sort. The meta-linked 3-BPT structures are particularly promising for their combined thermal properties and facile processability, and this concept adds value across a range of polymer materials that can accommodate BPT within the structure.

It is disclosed herein that BPT units can be integrated into cross-linked epoxy and cyanate ester networks, and the resulting materials represent significant improvement over existing materials. While most epoxy resins require added curing agents (e.g., multi-functional amines), cyanate ester (CE) resins cure thermally by cyclotrimerization to give polycyanurates (FIG. 5). As described below, these novel BPT-epoxies function effectively as one-component resins (i.e., requiring no curing catalyst), and that BPT-cyanate ester resins exhibit a markedly reduced gelation time (5 minutes at 170° C.) relative to more conventional versions of this class of materials.

BPT-Diglycidyl Ether Synthesis

Bisphenol triazoles 1' and 2', containing meta- and para-substitution patterns, respectively, were prepared by the click cycloaddition reactions reported previously. (Ryu, et al. 2010 *Angew. Chem. Int. Ed.* 49, 9644-9647) Then, the corresponding diglycidyl ether derivatives (DGE-BPTs) were prepared by reaction of the phenols with epichlorohydrin in a sodium hydroxide solution in water/isopropanol. 3-DGE-BPT, compound 3', was obtained as a yellow solid in 82% yield, and 4-DGE-BPT, compound 4', as a pale brown solid in 62% yield. Nuclear magnetic resonance (NMR) spectroscopy confirmed the desired structure of 3' and 4', as seen for example in the $^1$H NMR spectrum of 4' showing the characteristic glycidyl ether resonances centered at 4.35, 3.41, 2.97, and 2.82 ppm. Differential scanning calorimetry (DSC) analysis of 4-DGE-BPT showed a small endotherm at 190-195° C., and a large exotherm from 195-250° C. (FIG. 6), reflecting an initial melting that is followed immediately by self-curing. In contrast, 3-DGE-BPT 3' did not exhibit a clear melting point, showing only a glass transition at ~20° C., likely an effect of the meta-substitution. However, 3-DGE-BPT also showed a large exotherm from 160-280° C. upon self-curing. High resolution mass spectroscopy of 3' (366.1462 m/z of [M+H]$^+$) and 4' (366.1426 m/z of [M+H]$^+$) (calculated 366.1454 m/z), confirmed the expected molecular weight of each compound in fast atom bombardment (HRMS-FAB) mode. Interestingly, in electron impact mode (HRMS-EI), the expected signal at 365.14 m/z of [M]$^+$ was absent, but instead a signal at 337.13 m/z of [M–N$_2$]$^+$ was observed, due to the loss of N$_2$ from triazole under these ionization conditions.

Scheme 3

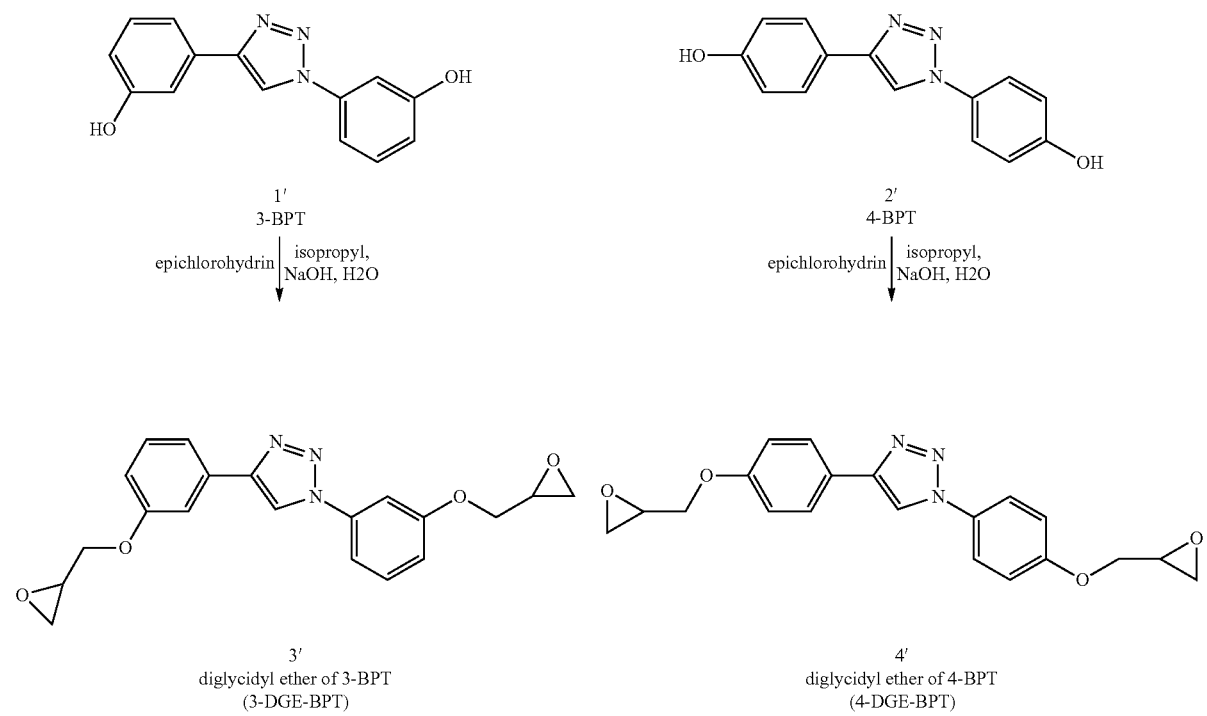

Scheme 4. Reaction of monoepoxide 6' with triazole 5'.

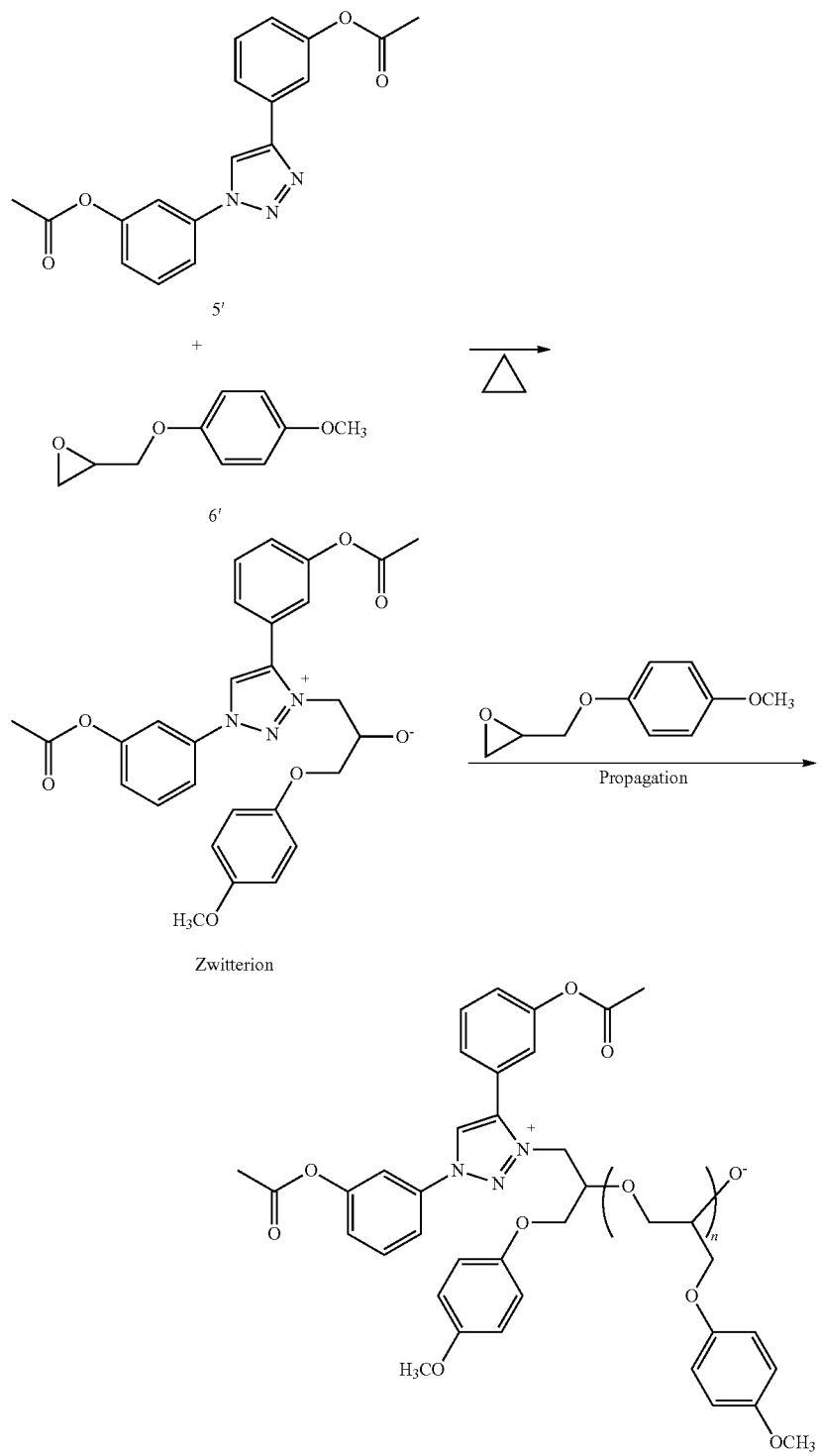

As the post-cured BPT-containing products are insoluble, and thus difficult to characterize by standard solution spectroscopy, the dimethyl ester version of BPT, shown as compound 5' in Scheme 4, was prepared for the purpose of examining its reaction with the aromatic monoglycidyl ether 6'. A mixture of 5' and 6' was heated to 180° C. for 1.5 hr, and the resulting reaction mixture was readily soluble and could be characterized by $^1$H-NMR spectroscopy. The glycidyl ether methylene and methyne resonances were absent, indicating the anticipated epoxide ring-opening, and new resonances from 4.43-4.05 ppm reflect the formation of an oligo(ethylene oxide) structure. The broadening of the triazole proton peak (from 8.22 ppm of 5' to 8.23-8.14 ppm in the product) suggests its reaction with the glycidyl ethers to give the zwitterionic structure shown in Scheme 4. As for curing with tertiary amines and imidazoles, the triazole moiety can attack the electron-poor methylene group of the epoxy moiety, giving a zwitterionic intermediate that is expected to propagate further to an oligomeric product. (Rozenberg 1986 *Adv. Polym. Sci.* 75, 146-156; Ricciardi, et al. 1983 *J. Polym. Sci. Polym. Chem. Ed.* 21, 1475-1490; Heise, et al. 1989 *Macromolecules* 22, 99-104.)

These novel DGE-BPT epoxy resins can be used alone in curing chemistry, or as a component of blends with other epoxides. Blends of DGE-BPT with BPA-based epoxy (DGE-BPA), and deoxybenzoin-based epoxy (DGE-BHDB), were prepared to determine the properties of these mixtures. (Ryu, et al. 2009 *Polymer* 50, 767-774.) By DSC, each blend showed a large exotherm in the temperature range of 160-320° C. (FIG. 7), due to catalytic curing at over 160° C. (regardless of para- or meta-substitution) under homogenous melt conditions.

The heat release and char properties of self-cured DGE-BPT resins and their blends with other diglycidyl ethers were characterized by pyrolysis combustion flow calorimetry (PCFC) and thermogravimetric analysis (TGA). Samples for PCFC and TGA were prepared by curing the homogenous mixture (in the melted state) for 2 h at 160° C., and for 1 h at 180° C., followed by a 1 h post-cure at 200° C. in a Teflon mold. The data obtained from these formulations are listed in Table 3. DGE-BHDB resins cured with the aromatic diamines diaminodiphenyl sulfone (DDS) and diaminodiphenyl methane (DDM) (Table 3, Entries 3 and 4) exhibited moderately lower heat release properties than those of the BPA version (Entry 1), due to the known char-forming properties of the deoxybenzoin moiety (increasing from 12% to 30-35%). (Ryu, et al. 2009 *Polymer* 50, 767-774; Ellzey, et al. 2006 *Macromolecules* 39, 3553-3558; Ranganathan, et al. 2006 *Macromolecules* 39, 5974-5975.) Impressively, despite the significant aliphatic character inherent to diglycidyl ethers, the HRC and THR values of the blended triazole containing resins (Entries 2, 5, 6, and 7) decreased significantly with increasing DGE-BPT content. The self-cured 3-DGE-BPT resin was most impressive in this regard, with a HRC of only 200±7 J/g-K, and an impressively high char value of 45%.

TABLE 3

Heat release and char properties of epoxy formulations.

| Entry | Formulation | HRC (J/g-K) | THR (kJ/g) | char (%)[b] |
|---|---|---|---|---|
| 1 | DGE-BPA/DDS[a] | 513 ± 10 | 25.3 ± 0.2 | 12 |
| 2 | DGE-BPA/3-DGE-BPT (1/1, w/w) | 408 ± 10 | 16.9 ± 0.2 | 26 |
| 3 | DGE-BHDB/DDS[a] | 420 ± 14 | 17.2 ± 0.2 | 30 |
| 4 | DGE-BHDB/DDM[a] | 439 ± 7 | 17.6 ± 0.2 | 35 |
| 5 | DGE-BHDB/4-DGE-BPT (4/1, w/w) | 265 ± 5 | 16.6 ± 0.4 | 35 |
| 6 | DGE-BHDB/3-DGE-BPT (1/1, w/w) | 222 ± 5 | 12.5 ± 0.2 | 43 |
| 7 | 3-DGE-BPT (self-cured) | 200 ± 7 | 10.9 ± 0.3 | 45 |

[a]Equivalent amount of aromatic diamine (DDS: diaminodiphenyl sulfone; DDM: diaminodiphenyl methane) was used (Ryu, et al. 2009 *Polymer* 50, 767-774.).
[b]Data obtained from TGA at 850° C. in nitrogen atmosphere (heating rate 10° C./min).

The adhesive properties of self-cured BPT-containing epoxies were confirmed by demonstrating adhesion of a metal alloy rod (30 g, 1 cm diameter) on a glass surface. The adhesion of the self-cured 3-DGE-BPT specimen was sufficiently robust to bear an additional 700 g loading (see FIG. 8). Quantitative adhesive studies (i.e., lap shear tests) of BPT-epoxy will be possible following development of these experimental scale materials into a larger scale process.

Bisphenol-1,2,3-triazole cyanate ester (BPTCE)

Combining the benefits of BPT with aryl cyanurate structures into a resin formulation would improve the conventional systems by reducing curing time and enhancing their flame resistance, even in the absence of added catalyst. The cyanate ester of 3-BPT (3-BPTCE, 7') was prepared in good yield by reaction of 3-BPT with cyanogen bromide in the presence of triethylamine (Scheme 5). 3-BPTCE was obtained as a pale brown solid, and seen to have a significantly higher melting point (155-160° C.) than the BPA version (78-82° C.). The $^{13}$C NMR spectrum of cyanate ester 7' showed signals at 108.6 and 108.9 ppm, in the expected regions for cyanate esters, with the two separate peaks arising as a consequence of the unsymmetrical nature of BPT (i.e., having a non-equivalent electronic environment around the two cyanate ester carbon atoms). Mass spectrometry analysis confirmed the desired structure, with BPTCE 7' giving a mass of 275.1 m/z by HRMS-EI ([M−N$_2$]$^+$) and 304.0822 m/z by HRMS-FAB ([M+H]$^+$, calculated 304.0834 m/z).

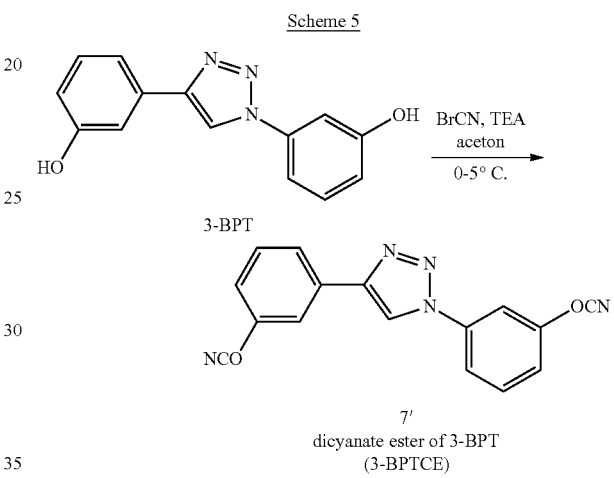

Scheme 5

7'
dicyanate ester of 3-BPT
(3-BPTCE)

Unlike BPA cyanate ester (BPACE), which requires implementation of heating cycles to achieve curing in the absence of added catalysts (e.g., 18 h at 150° C., 4 h 200° C., and 4 h 240° C.), BPTCE gelled rapidly after melting. Such rapid gelation of BPTCE allowed the curing reaction reach completion in 30 minutes, by heating the material from 160° C. to 280° C. at 5° C./min. Anticipating that BPTCE might be most useful in blends with commercially available BPACE, the effect of blend ratios on curing was investigated, in BPACE-to-BPTCE weight ratios of 9:1, 8:2, 7:3, and 1:1. Gelation times were measured using a magnetic stir bar (1 cm) in 100 mg of sample at 170° C., noting the time required for a mixture stirring initially at 200 rpm to stop completely (FIG. 9). At 170° C., BPACE alone showed no reduction in rpm for 6 h. However, for 9:1 and 7:3 BPACE:BPTCE blends, gelation time decreased dramatically from 230 min to 55 min, likely due to catalysis of the cyclotrimerization by the triazole group. (Nair, et al. 2001 *Adv. Polym. Sci.* 155, 1-99; Hamerton, (ed) 1994 *Chemistry and technology of cyanate ester resins*; Blackie Academic and Professional, Glasgow, UK.) Such mixtures may prove convenient for processes that require rapid on-line wetting, or continuous fiber reinforcement such as wet filament winding, resin transfer molding, and pultrusion. (Wallace, et al. 1992 U.S. Pat. No. 5,162,574.)

As a precursor to small scale flame tests, PCFC, and TGA experiments, BPACE/BPTCE blends were prepared by curing a homogenous mixture of the two cyanate esters for 4 h at 170° C., then for 4 h at 240° C., followed by post-curing at 280° C. for 1 h. BPACE samples were cured for 18 h at 150° C., then for 4 h at 200° C., 4 h at 240° C., and finally post-cured at 280° C. for 1 h. In the case of 3-BPTCE, samples were cured for 30 min at 170° C., then heated to 280° C. at 5° C./min. Small scale flame tests were conducted by placing a sample specimen (~1×0.35×0.1 cm) in a propane torch flame at a 45 degree angle for 3 seconds, noting the time required for the sample to self-extinguish following removal from the flame (FIG. 10). (Hergenrother, et al. 2005 *Polymer* 46, 5012-5024.) Striking differences were observed among these samples as a function of BPTCE content. BPACE exhibited self-sustained burning in air following removal from the flame, with moderate visible smoke. In the blended materials, intumescence increased with the BPTCE content, possibly due to $N_2$ gas evolution upon burning. Such intumescence can provide an effective barrier to release of fuel from the material surface. The specimens containing 50 wt % BPTCE (Entry 12) burned for only 1-2 sec, while BPTCE samples (Entry 13) were seen to extinguish immediately after removal from the flame, with little noticeable smoke evolution. BPTCE exhibited an impressive char volume, expanding outward from the specimen in the flame (FIGS. 10 (*c*) and (*d*)). Such char formation is exceptionally useful as it contributes further to effective suppression of flame spread.

The PCFC and TGA results of BPACE/BPTCE materials are listed in Table 4. Heat release values (HRC and THR values) of the cured blends decreased with increasing BPTCE weight percent, approximately following the rule of mixtures. Notably, the cured BPTCE exhibited miniscule HRC (10 J/g-K) and THR (2 kJ/g), extraordinary low values, even lower than halogen-containing CE resins such as hexafluoro-bisphenol A (62 J/g-K) HRC and 4.6 kJ/g THR) and bisphenol C containing CE resins (24 J/g-K HRC and 4.2 kJ/g THR). TGA of BPTCE showed a two-step weight loss curve (about 10% weight loss at 330-430° C.), which would be expected from the loss of $N_2$, and a 67% char yield at 850° C. (FIG. 11). With increasing BPT content in the blends, the slope of weight loss decreased and the residual mass (char) increased, indicating an enhanced flame-retardancy through char by aromatization during combustion.

TABLE 4

Heat release and char properties of cured BPACE, BPTCE, and blend resins.

| Entry | composition (w/w) | HRC (J/(g K)) | THR (kJ/g) | char (%)[a] |
|---|---|---|---|---|
| 8 | BPACE | 332 ± 10 | 14.5 ± 0.2 | 44 |
| 9 | BPACE/BPTCE (9/1) | 285 ± 14 | 13.4 ± 0.3 | 44 |
| 10 | BPACE/BPTCE (8/2) | 280 ± 15 | 12.5 ± 0.2 | 46 |
| 11 | BPACE/BPTCE (7/3) | 261 ± 12 | 11.2 ± 0.4 | 48 |
| 12 | BPACE/BPTCE (5/5) | 200 ± 15 | 9.2 ± 0.2 | 53 |
| 13 | BPTCE | 10 ± 2 | 2.0 ± 0.2 | 67 |

[a]Data obtained from TGA at 850° C. in nitrogen (heating rate 10° C./min).

Bisphenol-1,2,3-triazole polyphosphonate (BPTPP) and Epoxy Resin Blends

BPT polyphosphonate (BPTPP) was prepared in a similar manner as the polyarylates, using phenylphosphonic dichloride and benzyltriphenylphosphonium chloride instead of diacid chloride and benzyltriethylammonium chloride (Scheme 6). The BPTPP isolated from this reaction (~90% yield on ~1 gram scale) was found to be soluble in common organic solvents such as chloroform, dichloromethane, and N,N-dimethylformamide (DMF). The average molecular weights and polydispersity indices (PDI) were estimated by GPC in chloroform relative to polystyrene (PS) standard, for example giving a molecular weight of 13,900 g/mol $\overline{Mn}$, 33,320 g/mol $\overline{Mw}$, and 2.40 PDI. In PCFC, the polymer exhibited exceptionally low HRC of 96±2 J/g-K, THR of 8.6 kJ/g, and 50% char at 900° C.

Scheme 6

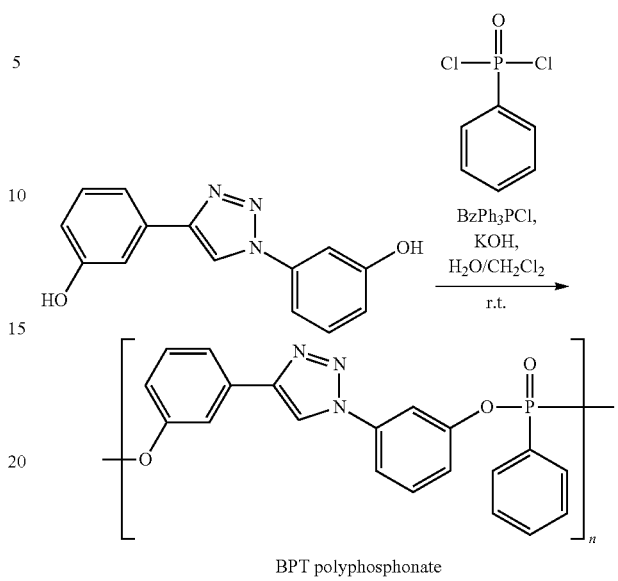

BPT polyphosphonate

The BPTPP blends with commercial bisphenol-A epoxy resin (DGE-BPA) and deoxybenzoin-based epoxy resin (DGE-BHDB) were prepared by mixing at 180° C. The homogeneous mixtures were cured for 3 h at 190° C., and post-cured for 2 h at 200° C. The PCFC and TGA results of BPTPP/epoxies are listed in Table 5. Despite the absence of aromatic diamines in the blends, HRC and THR values decreased with increasing BPTPP weight percent, regardless of epoxy resins. Especially, the DGE-BHDB blend cured with 20% BPTPP exhibited an approximate 300% reduction in HRC and THR from aromatic diamine cured resins. Such a dramatic reduction in heat release values may be due to the phosphorous-catalyzed char formation (38% char at 900° C.) with oxygen from BHDB in a condensed phase mechanism.

TABLE 5

Heat release and char properties of the cured epoxy resins.

| composition (w/w) | HRC (J/(g K)) | THR (kJ/g) | char (%) |
|---|---|---|---|
| DGE-BPA/DDS[a] | 513 ± 10 | 25.3 ± 0.2 | 12 |
| DGE-BPA/BPTPP 9/1 | 533 ± 7 | 19.2 ± 0.1 | 22 |
| DGE-BPA/BPTPP 8/2 | 466 ± 13 | 17.5 ± 0.1 | 28 |
| DGE-BHDB/DDS[a] | 420 ± 14 | 17.2 ± 0.2 | 30 |
| DGE-BHDB/BPTPP 9/1 | 188 ± 11 | 9.8 ± 0.3 | 38 |
| DGE-BHDB/BPTPP 8/2 | 125 ± 3 | 8.7 ± 0.3 | 44 |
| BPTPP | 96 ± 2 | 8.6 ± 0.2 | 50 |

[a]Equivalent amount of aromatic diamine (DDS: diaminodiphenyl sulfone) was used as a curing agent.

In summary, the invention disclosed herein provides the synthesis of novel bisphenol-triazole epoxy, cyanate ester resins, and polyphosphonate as self-catalyzed, self-extinguishing systems. BPT epoxy resins and their blends with BHDB epoxy are self-curable in the absence of aromatic diamines, and have significantly lower heat release properties than conventional non-halogenated versions. The presence of the BPT moiety in cyanate ester resins dramatically reduced the gelation time of blends relative to the conventional BPA version, and suppressed heat release properties and flammability. Most importantly, BPTCE, though halogen-free, clearly possesses ultra low heat release properties even lower than halogenated resins, and as such opens another opportunity for replacing halogenated molecules in many settings.

EXPERIMENTAL

Materials.

Ethynyltrimethylsilane (ETMS), pyridine, 4-iodophenol, 4-aminophenol, 3-iodophenol, 3-aminophenol, 2,2'-bipyridyl, sodium azide, sodium nitrite, N,N-diisopropylethylamine (DIPEA), copper bromide (CuBr), copper iodide (CuI), bis(triphenylphosphine)palladium(II) dichloride (PdCl$_2$(PPh$_3$)$_2$), deoxyanisoin, pyridine hydrochloride, epichlorohydrin, benzyltriphenylphosphonium chloride, phenylphosphonic dichloride, benzyltriethylammonium chloride, and cyanogen bromide were purchased from Sigma Aldrich and used without further purification. Bisphenol A cyanate ester (BPACE) was obtained from Lonza and used as received. Toluene, dichloromethane, and triethylamine were distilled prior to use. Silica gel (60 Å, 40-63 μm) was purchased from Sorbent Technologies.

Characterization.

$^1$H and $^{13}$C nuclear magnetic resonance (NMR) spectra were obtained on a Bruker DPX300 NMR spectrometer. Fourier transform infrared spectroscopy (FT-IR) was conducted on a Perkin-Elmer Spectrum One FT-IR spectrometer equipped with ATR accessory. High-resolution mass spectroscopy data (HRMS) of the final products were obtained on a JEOL JMS 700 mass spectrometer. Thermogravimetric analysis (TGA) was performed in nitrogen atmosphere on a DuPont TGA 2950 at a heating rate of 10° C./min. Char yields were determined by TGA from the mass residue at 850° C. Specific heat release rate (HRR, W/g), heat release capacity (HRC, J/g-K), and total heat release (THR, kJ/g) were measured by pyrolysis combustion flow calorimetery (PCFC) on 3-5 mg samples of cured resins. PCFC was conducted from 100 to 900° C. at a heating rate of 1° C./s in an 80 cm$^3$/min stream of nitrogen. The anaerobic thermal degradation products in the nitrogen gas stream were mixed with a 20 cm$^3$/min stream of oxygen prior to entering the combustion furnace (900° C.). The heat is determined by standard oxygen consumption methods. During the test, HRR is obtained by dividing dQ/dt, at each time interval, by the initial sample mass, and HRC is obtained by dividing the maximum value of HRR by the heating rate. Three-to-five sample runs were conducted for each sample.

Synthesis of BPT-Based Resins and BHDB-Based Epoxy Resin (DGEBHDB)

1,4-Bis(3-hydroxyphenyl)-1,2,3-triazole (3-BPT), 1,4-bis(4-hydroxyphenyl)-1,2,3-triazole (4-BPT), diglycidyl ether of 4,4'-bishydroxydeoxybenzoin (DGE-BHDB) were prepared according to literature (Ryu, et al. 2010 *Angew. Chem. Int. Ed.* 49, 9644-9647; Ryu, et al. 2009 *Polymer* 50, 767-774; Ellzey, et al. 2006 *Macromolecules* 39, 3553-3558; Ranganathan, et al. 2006 *Macromolecules* 39, 5974-5975.)

3-Azidophenol

An aqueous solution (15 mL) of NaNO$_2$ (3.79 g, 54.98 mmol) was added dropwise to 3-aminophenol (5.0 g, 45 mmol) in 2 N HCl (100 mL) at 0-5° C. The solution was stirred for 30 minutes, followed by addition of an aqueous solution of sodium azide (4.5 g, 69 mmol, in 35 mL water). The mixture was stirred at room temperature for 24 h, and extracted with 300 mL of ethyl acetate. The combined organic layer was washed with water, and dried over MgSO$_4$. Solvents were removed by rotary evaporation, and the residue was purified by column chromatography (EtOAc/hexanes, 1/4) to give the desired product as a dark red oil (4.52 g, 73% yield): $^1$H NMR (acetone-d$_6$, 300 MHz, ppm): 8.69 (s, 1H, Ar—OH), 7.24 (t, 1H, J=8.1 Hz, Ar—H), 6.70-6.53 (m, 3H, Ar—H). $^{13}$C NMR (CDCl$_3$, 75 MHz, ppm): 157.2, 141.6, 130.9, 112.4, 111.5, 106.5. FT-IR (cm$^{-1}$): 3348, 2109.

4-Azidophenol

4-Azidophenol was prepared similarly to 3-azidophenol, using 4-aminophenol (5.0 g) instead of 3-aminophenol. This gave 5.27 g (85% yield) of a dark red oil. $^1$H NMR (acetone-d$_6$, 300 MHz, ppm): 8.48 (s, 1H, Ar—OH), 6.94 (m, 4H, Ar—H). $^{13}$C NMR (MeOD-d$_4$, 75 MHz, ppm): 156.4, 132.4, 121.1, 117.7. FT-IR (cm$^{-1}$): 3372, 2113, 2072.

3-(2-trimethylsilylethynyl)phenol (3-TMSE-phenol)

To 3-iodophenol (5.0 g, 23 mmol) in 50 mL of toluene were added PdCl$_2$(PPh$_3$)$_2$ (479 mg, 689 μmol), CuI (432 mg, 2.27 mmol), DIPEA (4.8 mL, 27 mmol), and ETMS (3.90 mL, 27.3 mmol). The mixture was stirred at 30° C. for 24 h, then cooled to room temperature. After filtering, solvents were removed by rotary evaporation. The residue was purified by column chromatography (EtOAc/hexane, 1/9) to give 4.1 g (95% yield) of a brown oil. $^1$H NMR (acetone-d$_6$, 300 MHz, ppm): 8.57 (s, 1H, Ar—OH), 7.02 (m, 1H, Ar—H), 6.96-6.86 (m, 3H, Ar—H), 0.23 (s, 9H, TMS), $^{13}$C NMR (CDCl$_3$, 75 MHz, ppm): 155.5, 129.8, 124.8, 124.4, 118.8, 116.3, 105.0, 94.5, 0.1.

4-(2-trimethylsilylethynyl)phenol (4-TMSE-phenol)

4-TMSE-phenol was prepared in a similar manner as 3-TMSE-phenol, using 4-iodophenol (5.0 g) instead of 3-iodophenol. This gave 3.5 g (82% yield) of a brown oil. $^1$H NMR (acetone-d$_6$, 300 MHz, ppm): 8.80 (s, 1H, Ar—OH), 7.34 (d, 2H, J=8.4 Hz, Ar—H), 6.85 (d, 2H, J=8.4 Hz, Ar—H), 0.21 (s, 9H, TMS). $^{13}$C NMR (CDCl$_3$, 75 MHz, ppm): 156.1, 133.9, 115.6, 115.5, 105.3, 92.7, 0.2.

1,4-Bis(3-hydroxyphenyl)-1,2,3-triazole (3-BPT)

To 3-TMSE-phenol (4.0 g, 21.02 mmol) in 35 mL of DMF were added 3-azidophenol (3.41 g, 25.2 mmol), CuBr (153 mg, 1.05 mmol), and 2,2'-bipyridyl (328 mg, 2.10 mmol). The mixture was heated at 80° C. for 24 h, cooled to room temperature, then diluted with 250 mL of EtOAc. The combined organic mixture washed with water, and dried over MgSO$_4$. Solvents were removed by rotary evaporation, and the residue was recrystallized in acetic acid/water to give 3.70 g (70% yield) of a brown crystalline solid. $^1$H NMR (MeOD-d$_4$, 300 MHz, ppm): 8.80 (s, 1H, triazol-H), 7.43-7.26 (m, 6H, Ar—H), 6.95-6.91 (m, 1H, Ar—H), 6.84-6.83 (m, 1H, Ar—H). $^{13}$C NMR (MeOD-d$_4$, 75 MHz, ppm): 158.6, 157.7, 148.1, 137.9, 131.1, 130.4, 129.7, 118.8, 116.7, 115.6, 115.1, 112.1, 110.7, 107.1.

1,4-Bis(4-hyroxyphenyl)-1,2,3-triazole (4-BPT)

4-BPT was prepared in a similar manner as 3-BPT, using 4-TMSE-phenol (3.50 g, 18.4 mmol) and 4-azidophenol (3.73 g, 27.9 mmol) instead of 3-TMSE-phenol and 3-azidophenol. This gave 2.79 g (60% yield) of a purple crystal. $^1$H NMR (MeOD-d$_4$, 300 MHz, ppm): 8.62 (s, 1H, triazol-H), 7.75-7.68 (m, 4H, Ar—H), 6.99 (d, 2H, J=9.0 Hz, Ar—H), 6.90 (d, 2H, J=8.7 Hz, Ar—H). $^{13}$C NMR (MeOD-d$_4$, 75 MHz, ppm): 159.7, 159.3, 149.8, 131.0, 128.4, 123.4, 123.0, 119.4, 117.3, 116.9.

4,4'-Bishydroxydeoxybenzoin (BHDB)

Desoxyanisoin (5.00 g, 19.5 mmol) and pyridine hydrochloride (9.02 g, 78.0 mmol) were added to a round-bottom flask equipped with a condenser. The mixture was refluxed for 5 h at 200° C., cooled to room temperature, and poured into water. The precipitate was filtered and recrystallized from acetic acid to give 3.8 g (85% yield) of a pale yellow crystalline solid. $^1$H NMR (DMSO-d$_4$, 300 MHz, ppm): 10.35 (s, 1H, HO—Ar—CO), 9.28 (s, 1H, HO—Ar—CH$_2$), 7.91 (d, 2H, J=8.7 Hz, Ar—H), 7.04 (d, 2H, J=8.5 Hz, Ar—H), 6.84 (d, 2H, J=8.7 Hz, Ar—H), 6.68 (d, 2H, J=8.5 Hz, Ar—H), 4.11 (s, 2H, Ar—CO—CH$_2$—Ar). $^{13}$C NMR (DMSO-d$_6$, 75 MHz, ppm): 196.5, 162.3, 156.2, 131.3, 130.7, 128.1, 125.9, 115.5, 115.4, 43.7.

Diglycidyl ether of 4,4'-bishydroxydeoxybenzoin (DGE-BHDB)

Epichlorohydrin (5.0 g, 54 mmol), BHDB (1.24 g, 5.43 mmol), 2-propanol (2.7 g, 4.5 mmol), and water (0.43 mL) were added to a round-bottom flask and stirred at 65° C. A 20% aqueous sodium hydroxide solution (1.95 g) was added dropwise over 45 min, and stirring was continued for 30 min. The mixture was cooled to room temperature, and chloroform (50 mL) was added. The organic layer was washed extensively with water, and the combined organic extract was dried over magnesium sulfate. Solvents were removed by rotary evaporation, and the residue was dissolved in chloroform then precipitated into hexanes to give 1.48 g (80% yield) of the product as a pale yellow solid. $^1$H-NMR (CDCl$_3$, 300 MHz, ppm): 7.99 (d, 2H, J=8.8 Hz, Ar—H), 7.18 (d, 2H, J=8.4 Hz Ar—H), 6.91 (d, 2H, J=8.8 Hz, Ar—H), 6.88 (d, 2H, J=8.4 Hz, Ar—H), 4.32-4.17 (m, 2H, 2(—O—CH$_2$-Oxirane)), 4.17 (s, 2H, Ar—CO—CH$_2$—Ar), 4.01-3.92 (m, 2H, 2(—O—CH$_2$-Oxirane)), 3.39-3.32 (m, 2H, 2(Oxirane CH)), 2.94-2.88 (m, 2H, 2(Oxirane CH$_2$)), 2.78-2.74 (m, 2H, 2(Oxirane CH$_2$)). $^{13}$C-NMR (CDCl$_3$, 75 MHz, ppm): 196.5, 162.3, 157.4, 130.9, 130.5, 130.0, 127.5, 114.8, 114.4, 68.9, 68.8, 50.2, 49.9, 44.7, 44.6, 44.4. HRMS-EI m/z [M]$^+$ calcd. 340.1311; found 340.1293.

Diglycidyl ether of 1,4-bis(3-hydroxyphenyl)-1,2,3-triazole (3-DGE-BPT)

3-DGE-BPT was prepared in a similar manner as DGE-BHDB, using 3-BPT (1.00 g, 39.5 mmol) instead of BHDB. This gave 1.18 g (82% yield) of a yellow amorphous solid. $^1$H NMR (CDCl$_3$, 300 MHz, ppm): 8.19 (s, 1H, triazol-H), 7.55-7.36 (m, 6H, Ar—H), 7.05-6.94 (m, 2H, Ar—H), 4.41-4.33 (m, 2H, 2(—O—CH$_2$-Oxirane)), 4.05-4.01 (m, 2H, 2(—O—CH$_2$-Oxirane)), 3.42-3.41 (m, 2H, 2(Oxirane CH)), 2.96-2.95 (m, 2H, 2(Oxirane CH$_2$)), 2.82-2.81 (m, 2H, 2(Oxirane CH$_2$)). $^{13}$C-NMR (CDCl$_3$, 75 MHz, ppm): 161.1, 160.6, 149.7, 139.6, 133.1, 132.3, 131.7, 120.3, 119.4, 116.8, 114.5, 113.2, 108.6, 70.8, 70.4, 51.7, 51.6, 46.3, 46.2. HRMS-FAB m/z [M+H]$^+$ calcd. 366.1454; found 366.1462.

Diglycidyl ether of 1,4-bis(4-hydroxyphenyl)-1,2,3-triazole (4-DGE-BPT)

4-DGE-BPT was prepared in a similar manner as DGE-BHDB, using 4-BPT (1.00 g, 39.5 mmol) instead of BHDB. This gave 890 mg (62% yield) of a pale purple solid. $^1$H NMR (CDCl$_3$, 300 MHz, ppm): 8.06 (s, 1H, triazol-H), 7.86 (d, 2H, J=8.7 Hz, Ar—H), 7.72 (d, 2H, J=9.0 Hz, Ar—H), 7.11 (d, 2H, J=9.0 Hz, Ar—H), 7.05 (d, 2H, J=8.7 Hz, Ar—H), 4.38-4.29 (m, 2H, 2(—O—CH$_2$-Oxirane)), 4.06-3.99 (m, 2H, 2(—O—CH$_2$-Oxirane)), 3.42-3.41 (m, 2H, 2(Oxirane CH)), 2.99-2.95 (m, 2H, 2(Oxirane CH$_2$)), 2.84-2.81 (m, 2H, 2(Oxirane CH$_2$)). $^{13}$C-NMR (CDCl$_3$, 75 MHz, ppm): 158.7, 158.6, 147.9, 130.9, 127.3, 123.5, 122.3, 117.4, 115.7, 115.2, 69.2, 68.9, 50.3, 50.2, 44.8, 44.7. HRMS-FAB m/z [M+H]$^+$ calcd. 366.1454; found 366.1426.

Dicyanate ester of 1,4-bis(3-hydroxyphenyl)-1,2,3-triazole (3-BPTCE)

1.89 mL of cyanogen bromide (1.00 g, 94.8 mmol) as a molar solution in acetonitrile was added to 3-BPT (1.00 g, 39.5 mmol) in 60 mL of acetone at 0-5° C. After stirring for 20 min, triethyl amine (1.16 mL, 82.9 mmol) was added dropwise at 0-5° C. The mixture was stirred for 1 h, and diluted with 200 mL of dichloromethane. The combined organic mixture was washed with 10% aqueous Na$_2$CO$_3$ solution and water. Solvents in the organic extract were removed by rotary evaporation, and the precipitate was washed with methanol to give 1.08 g (90% yield) of the desired product as a pale brown solid. $^1$H NMR (DMSO-d$_6$, 300 MHz, ppm): 9.36 (s, 1H, triazol-H), 8.05 (m, 4H, Ar—H), 7.88 (m, 1H, Ar—H), 7.71 (m, 1H, Ar—H), 7.63-7.59 (m, 1H, Ar—H) 7.46-7.42 (m, 1H, Ar—H). $^{13}$C NMR (DMSO-d$_6$, 75 MHz, ppm): 153.5, 153.4, 146.3, 138.2, 133.1, 133.0, 132.2, 124.3, 121.5, 118.7, 116.1, 115.7, 112.2, 108.9, 108.6, 108.1. HRMS-FAB m/z [M+H]$^+$ calcd. 304.0834; found 304.0822.

Interfacial Polymerization.

All polymers were prepared in the same manner by following procedure. To 3-BPT (125 mg, 493.6 μmol), BPA (113 mg, 493.6 μmol), and Et$_3$BzNCl (15 mg, 131.7 μmol) in 5 mL of 1 M NaOH aqueous solution was added isophthaloyl dichloride (201 mg, 987.2 μmol) in DCM. The two-phase mixture was stirred vigorously for 2 h, and poured into methanol. The precipitate was filtered, and washed with hot water and methanol to give 310 mg (85% yield) of a film-like solid. $^1$H NMR (300 MHz, [D$_2$]TCE): δ=8.98 (m, 2H; isophthaloyl Ar—H), 8.47 (m, 4H; isophthaloyl Ar—H) 8.30 (s, 1H; triazol-H), 7.83-7.30 (m, 14H; isophthaloyl, BPA, and BPT Ar—H), 7.19 (d, J=7.5 Hz, 4H; BPA Ar—H), 1.75 ppm (s, 6H; BPA-methyl). Yield of 3-BPT, 4-BPT, 4-BPT/BPA (50/50), and BPTPP were 88, 64, 84%, and 90% respectively.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance which can be adapted to the practice of this invention in its various embodiments and equivalents thereof.

The invention claimed is:

1. A polymer comprising a structural unit of:

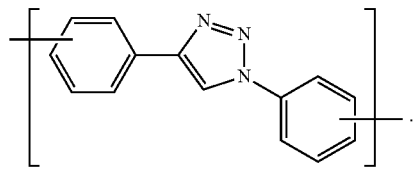

2. The polymer of claim 1, wherein the structural unit is:

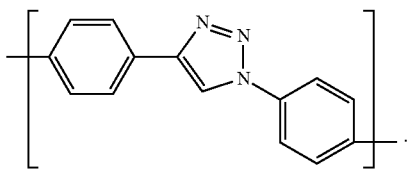

3. The polymer of claim 1, wherein the structural unit is:

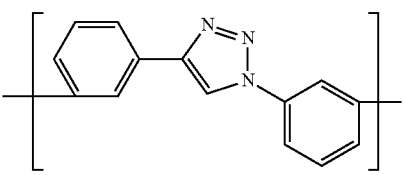

4. The polymer of claim 1, further comprising the structural unit of:

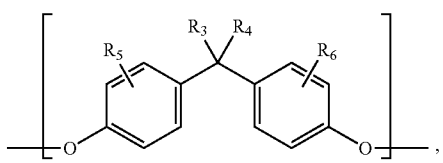

wherein
- each of $R_3$ and $R_4$ is independently selected from hydrogen, unsubstituted $C_1$-$C_4$ alkyl, —$CF_3$, phenyl, and benzyl;
- each of $R_5$ and $R_6$ is independently selected from hydrogen, unsubstituted $C_1$-$C_4$ alkyl, phenyl, and benzyl.

5. The polymer of claim 4, wherein each of $R_3$ and $R_4$ is methyl and $R_5$ and $R_6$ is hydrogen

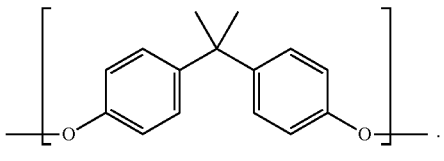

6. The polymer of claim 1, further comprising a bi-radical group based on a bisphenol selected from Table 1.

7. The polymer of claim 4, further comprising the structural unit of:

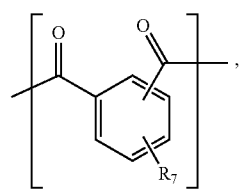

wherein $R_7$ is selected from hydrogen, unsubstituted $C_1$-$C_4$ alkyl, —$CF_3$, phenyl, and benzyl.

8. The polymer of claim 7, wherein $R_7$ is hydrogen.

9. The polymer of claim 8, wherein the structural unit is:

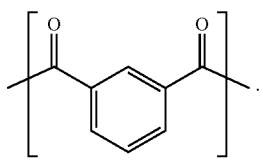

10. The polymer of claim 4, further comprising the structural unit of:

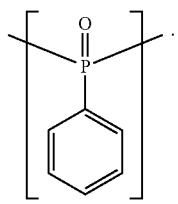

11. The polymer of claim 7, wherein the molar ratio of

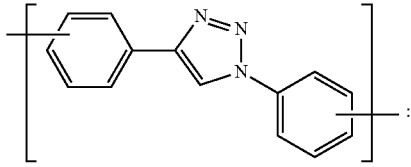

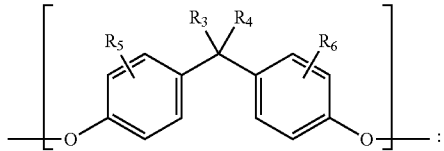

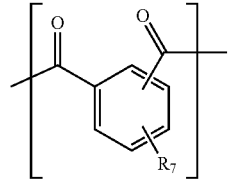

is in the range from about 1:4:5 to about 4:1:5.

12. The polymer of claim 2, comprising the structural unit of:

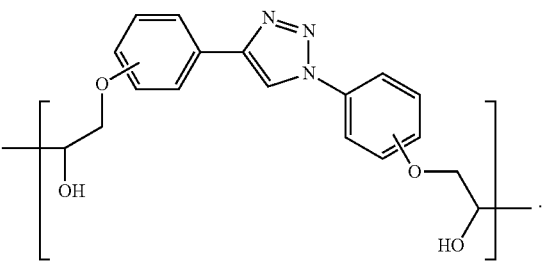

13. A co-polymer having the structural formula of:
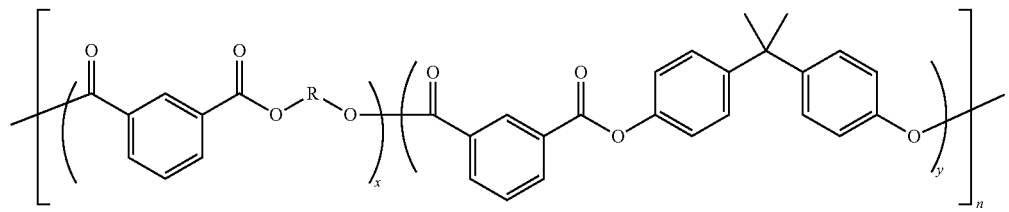
wherein R is
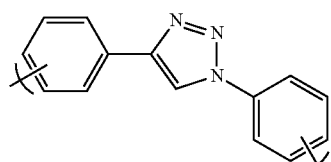
y is 0 or the x:y molar ratio is in the range from about 0.1:0.9 to about 0.9:0.1 (x+y=1); and
n is from about 2 to about 200,
wherein the co-polymer is a random copolymer.
14. The co-polymer of claim 13, wherein R is
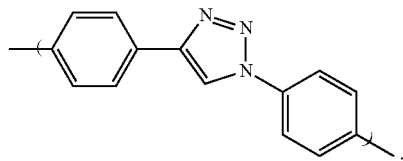
15. The co-polymer of claim 13, wherein R is
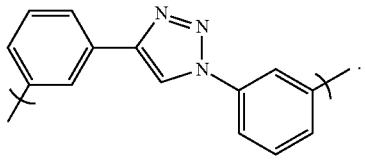
16. The co-polymer of claim 13, wherein y is zero.
17. The co-polymer of claim 13, wherein y is 0.5.